US012667672B2

(12) United States Patent
Schabbach

(10) Patent No.: US 12,667,672 B2
(45) Date of Patent: Jun. 30, 2026

(54) DOSAGE MEASUREMENT SYSTEM

(71) Applicant: SANOFI, Paris (FR)

(72) Inventor: Michael Schabbach, Frankfurt am Main (DE)

(73) Assignee: SANOFI, Paris (FR)

( * ) Notice: Subject to any disclaimer, the term of this patent is extended or adjusted under 35 U.S.C. 154(b) by 786 days.

(21) Appl. No.: 16/958,434

(22) PCT Filed: Dec. 20, 2018

(86) PCT No.: PCT/EP2018/086102
§ 371 (c)(1),
(2) Date: Jun. 26, 2020

(87) PCT Pub. No.: WO2019/129621
PCT Pub. Date: Jul. 4, 2019

(65) Prior Publication Data
US 2021/0052819 A1     Feb. 25, 2021

(30) Foreign Application Priority Data

Dec. 28, 2017     (EP) ..................................... 17306953

(51) Int. Cl.
*A61M 5/315*         (2006.01)
*A61M 5/20*          (2006.01)
*A61M 5/31*          (2006.01)
(52) U.S. Cl.
CPC .... *A61M 5/31568* (2013.01); *A61M 5/31585* (2013.01); *A61M 5/20* (2013.01);
(Continued)
(58) Field of Classification Search
None
See application file for complete search history.

(56) References Cited

U.S. PATENT DOCUMENTS 11,612,698 B2 * 3/2023 Katuin .............. A61M 5/31581
604/246
2012/0268741 A1 10/2012 Pommereau et al.
(Continued)

FOREIGN PATENT DOCUMENTS

CN         101909673         12/2010
CN         102307611         1/2012
(Continued)

OTHER PUBLICATIONS

PCT International Preliminary Report on Patentability in International Appln. No. PCT/EP2018/086102, dated Jun. 30, 2020, 10 pages.

(Continued)

*Primary Examiner* — Bhisma Mehta
*Assistant Examiner* — Mark A Igel
(74) *Attorney, Agent, or Firm* — Bond Schoeneck & King PLLC

(57) ABSTRACT

The disclosure relates to a dosage measurement system for a medicament delivery device. The medicament delivery device includes a medicament reservoir and a dispensing mechanism. The dispensing mechanism includes a dispensing member that is moveable axially to dispense medicament from the medicament reservoir. The dosage measurement system includes a sensor unit and a processor. The sensor unit is configured to measure the axial displacement of the dispensing member. The processor is configured to determine a dosage dispensed from the medicament reservoir based on the measured axial displacement of the dispensing member.

18 Claims, 14 Drawing Sheets

(52) U.S. Cl.
CPC ............... *A61M 2005/3126* (2013.01); *A61M 2205/3306* (2013.01); *A61M 2205/3317* (2013.01); *A61M 2205/3375* (2013.01); *A61M 2205/52* (2013.01); *A61M 2205/581* (2013.01); *A61M 2205/582* (2013.01); *A61M 2205/583* (2013.01); *A61M 2205/8206* (2013.01)

(56) References Cited

U.S. PATENT DOCUMENTS

| | | | | |
|---|---|---|---|---|
| 2013/0197445 A1* | 8/2013 | Schabbach | ............. | G16H 20/17 |
| | | | | 604/189 |
| 2015/0202386 A1* | 7/2015 | Brady | ............... | A61M 5/31573 |
| | | | | 324/207.2 |
| 2015/0320934 A1* | 11/2015 | Draper | .................... | G01D 5/32 |
| | | | | 604/154 |
| 2017/0136185 A1* | 5/2017 | Rios | ................... | A61M 5/31511 |
| 2017/0151392 A1* | 6/2017 | Marsh | ............... | A61M 5/31585 |
| 2017/0182251 A1* | 6/2017 | Nagel | ................. | A61M 5/1684 |
| 2017/0189625 A1* | 7/2017 | Cirillo | ................. | A61M 5/3155 |
| 2017/0246399 A1* | 8/2017 | Forlani | ................... | A61M 5/20 |
| 2018/0042462 A1* | 2/2018 | Yanuma | ............. | A61B 1/00098 |
| 2018/0078711 A1* | 3/2018 | Krasnow | ............... | G01F 11/027 |
| 2020/0230325 A1* | 7/2020 | Bengtsson | ........ | A61M 5/31568 |
| 2024/0157045 A1* | 5/2024 | Kostal | ............... | A61M 5/31513 |

FOREIGN PATENT DOCUMENTS

| | | | | |
|---|---|---|---|---|
| CN | 103458940 | | 12/2013 | |
| CN | 104114211 | | 10/2014 | |
| CN | 104428688 | | 3/2015 | |
| CN | 106456884 | | 2/2017 | |
| CN | 106659848 | | 5/2017 | |
| CN | 107405449 | | 11/2017 | |
| EP | 3058970 | | 8/2016 | |
| EP | 3067081 | A1 * | 9/2016 | ........ A61M 5/31593 |
| JP | 2013-505433 | | 2/2013 | |
| JP | 2014-531283 | | 11/2014 | |
| JP | 2015-529481 | | 10/2015 | |
| JP | 2017-508596 | | 3/2017 | |
| WO | WO 2009/083600 | | 7/2009 | |
| WO | WO 2010/088973 | | 8/2010 | |
| WO | WO 2011/032960 | | 3/2011 | |
| WO | WO 2012/140052 | | 10/2012 | |
| WO | WO 2013/050535 | | 4/2013 | |
| WO | WO 2013/096713 | | 6/2013 | |
| WO | WO 2013/096722 | | 6/2013 | |
| WO | WO 2014/009442 | | 1/2014 | |
| WO | WO 2015/136513 | | 9/2015 | |
| WO | WO 2015/143058 | | 9/2015 | |
| WO | WO 2016/001300 | | 1/2016 | |
| WO | WO 2016/036574 | A1 | 3/2016 | |
| WO | WO 2016/142511 | | 9/2016 | |
| WO | WO 2017/070391 | | 4/2017 | |

OTHER PUBLICATIONS

PCT International Search Report and Written Opinion in International Appln. No. PCT/EP2018/086102, dated Mar. 4, 2019, 15 pages.

Office Action, JP Patent Application No. 2023-187350, dated Aug. 13, 2024, pp. 1-7 with pp. 1-4 being a translation.

* cited by examiner

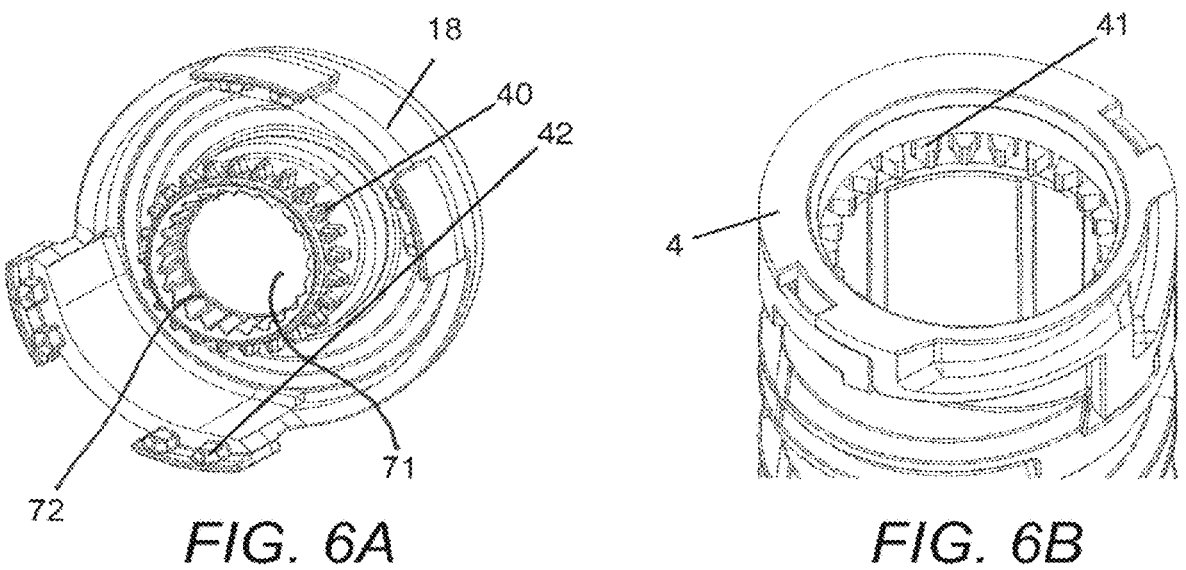
*FIG. 6A*
*FIG. 6B*
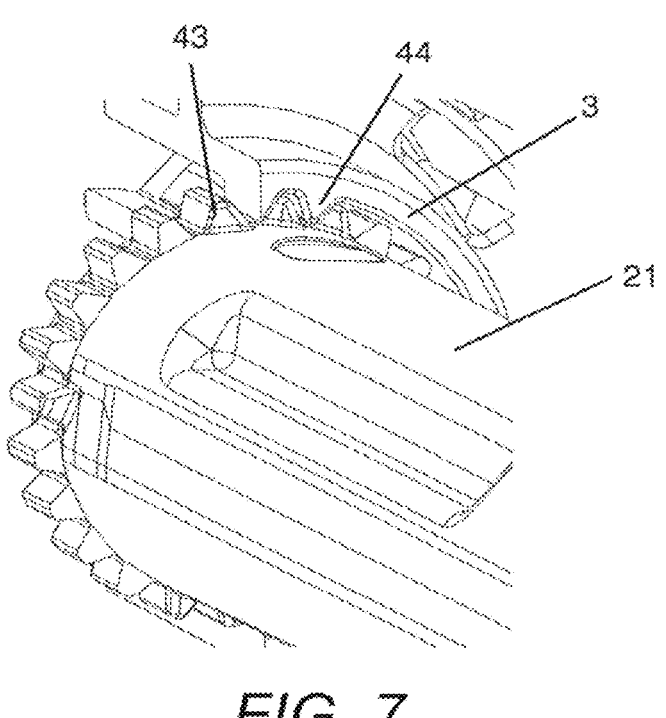
*FIG. 7*

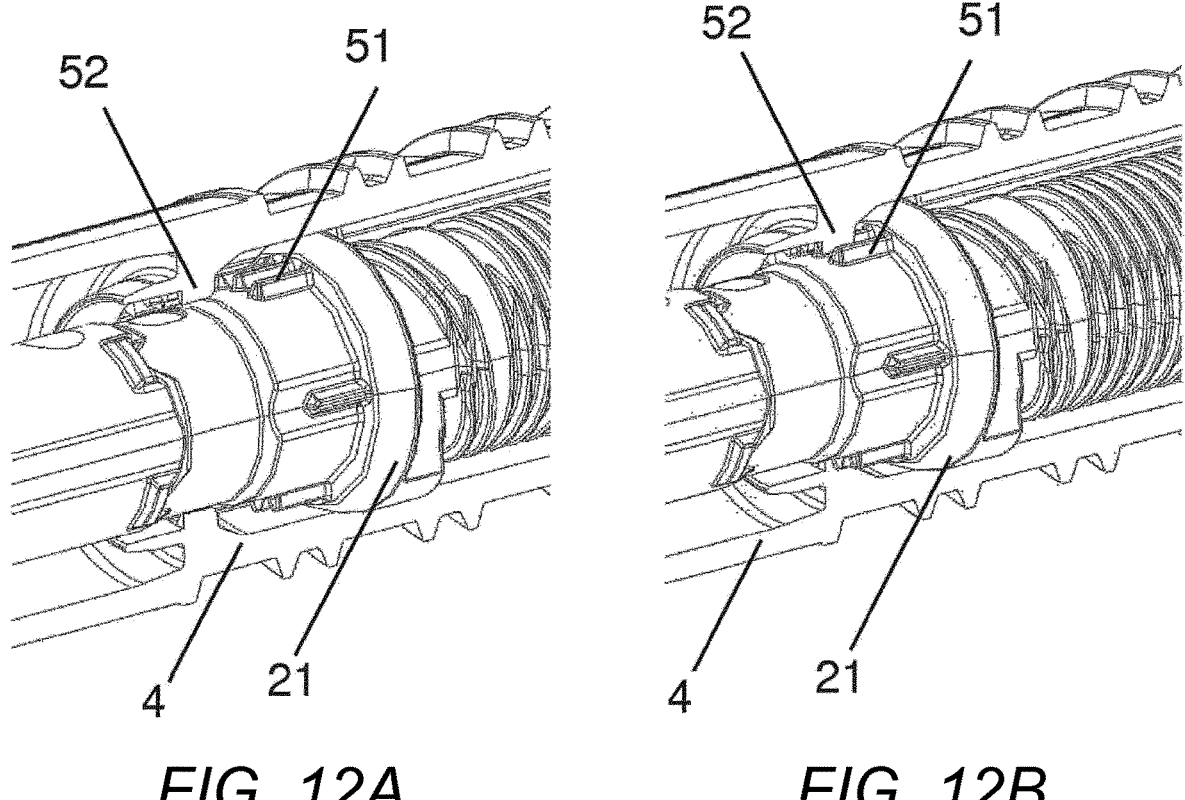
*FIG. 12A*          *FIG. 12B*
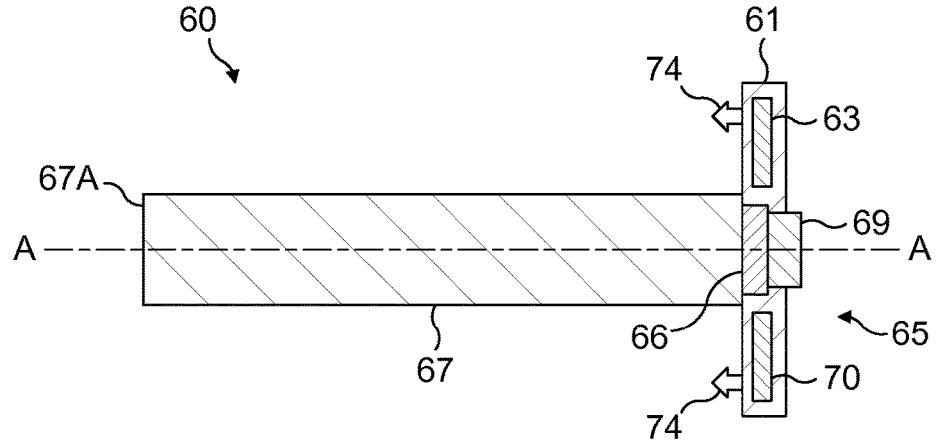
*FIG. 13*

DOSAGE MEASUREMENT SYSTEM

CROSS REFERENCE TO RELATED APPLICATIONS

The present application is the national stage entry of International Patent Application No. PCT/EP2018/086102, filed on Dec. 20, 2018, and claims priority to Application No. EP 17306953.5, filed on Dec. 28, 2017, the disclosures of which are incorporated herein by reference.

TECHNICAL FIELD

The present disclosure is generally related to a dosage measurement system. The present disclosure also relates to a dosage measurement device, a medicament delivery system, and to a method of determining a dosage of medicament dispensed from a medicament delivery device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose.

SUMMARY

An aspect of the present disclosure is to provide an improved dosage measurement system, dosage measurement device, medicament delivery system, and method of determining a dosage of medicament dispensed from a medicament delivery device.

According to the present disclosure, there is provided a dosage measurement system for a medicament delivery device, wherein the medicament delivery device comprises a medicament reservoir and a dispensing mechanism comprising a dispensing member that is moveable axially to dispense medicament from the medicament reservoir, the dosage measurement system comprising: a sensor unit configured to measure the axial displacement of the dispensing member; and, a processor configured to determine a dosage dispensed from the medicament reservoir based on the measured axial displacement of the dispensing member.

In some embodiments, the sensor unit may be attached to the end of an existing medicament delivery device without requiring major modification of the medicament delivery device. For instance, if the existing medicament delivery device has a dispensing member comprising a lead screw then the sensor unit may be attached to, for example, the proximal end of the medicament delivery device to measure the axial displacement of the lead screw.

The sensor unit may be configured to be located such that the dispensing member moves away from the sensor unit to dispense medicament from the medicament reservoir.

In one embodiment, the sensor unit is configured to transmit a signal such that said signal is reflected from the dispensing member, wherein the sensor unit is configured to detect said reflected signal. In one embodiment, the sensor unit is configured such that the signal is reflected from a proximally facing surface of the lead screw.

In one embodiment, the sensor unit comprises a transmission member, said signal being transmitted through the transmission member. Thus the transmission member helps to direct the signal towards the dispensing member. Therefore, the sensor itself does not need to be positioned in proximity to the dispensing member. The transmission member may comprise a light guide.

In one embodiment, the dispensing member comprises a lead screw and wherein the dispensing mechanism further comprises a drive member that is configured to rotate to axially displace the lead screw relative to the drive member to dispense medicament from the medicament reservoir. The sensor may thus be provided axially aligned with the lead screw to reduce the radial dimensions of the medicament delivery device.

In one embodiment, the sensor unit is configured to transmit a signal that travels within the drive member. The drive member may be a drive sleeve. The drive sleeve may comprise a generally cylindrical peripheral wall.

The dispensing member may be a component that is moveable axially relative to the housing to dispense medicament from the medicament reservoir.

In one embodiment, the sensor unit is integrated with the medicament delivery device.

In one embodiment, the sensor unit is removably attachable to the medicament delivery device. Therefore, the medicament delivery device can be disposed of and the sensor unit detached from the medicament delivery device for re-use prior to disposal of the medicament delivery device.

In one embodiment, the sensor unit comprises at least one of an optical sensor, a magnetic sensor, an acoustic sensor or a capacitive sensor.

In one embodiment, the sensor unit is configured such that said signal is reflected from an end of the dispensing member. The sensor unit may be configured such that the signal is reflected from a proximally-facing surface of the dispensing member. Thus, the sensor unit may be positioned on the proximal side of the dispensing member to reduce the radial dimension of the device.

In one embodiment, the dosage measurement system comprises a display. The display may be configured to display dosage information.

In one embodiment, the medicament delivery device comprises an actuator that is actuatable by a user to dispense medicament, and wherein the sensor unit is configured to be mounted to the actuator. The actuator may comprise a space, wherein the sensor unit is configured to be at least partially received in the space.

In one embodiment, the actuator is configured to move from a first position to a second position upon actuation, and wherein the sensor unit is configured to be mounted to the actuator to move with the actuator between the first and second positions. In one such embodiment, the processor is configured to only determine the dosage dispensed from the medicament reservoir when the actuator is in the second position.

In one embodiment, the dosage measurement system is configured such that the processor only determines the dosage dispensed from the medicament reservoir when the actuator is actuated. This helps to prevent the processor from providing inaccurate dosage information.

In one embodiment, the dosage measurement system comprises a first part configured to be fixed to a medicament delivery device and a second part that is removably attachable to the first part. The second part may comprise the processor. Thus, the first part may be disposed of with the medicament delivery device and the second part may be attached to the first part of a further medicament delivery device and re-used. In one embodiment, the first part comprises the transmission member.

According to the present disclosure, there is also provided a dosage measurement device comprising a dosage measurement system according to the disclosure.

According to the present disclosure, there is also provided a medicament delivery system comprising: a medicament delivery device comprising a medicament reservoir and a dispensing mechanism comprising a dispensing member that is moveable axially to dispense medicament from the medicament reservoir; and, a dosage measurement system according to the disclosure. The medicament reservoir may contain medicament.

According to the present disclosure, there is also provided a method of determining a dosage of medicament dispensed from a medicament delivery device, wherein the medicament delivery device comprises a medicament reservoir and a dispensing member that is moveable axially to dispense medicament from the medicament reservoir, the method comprising: measuring the axial displacement of the dispensing member; and, determining the dosage dispensed from the medicament reservoir based on the measured axial displacement of the dispensing member.

In one embodiment, the dispensing member comprises a lead screw and wherein the dispensing mechanism further comprises a drive member that is configured to rotate to axially displace the lead screw relative to the drive member to dispense medicament from the medicament reservoir. In one embodiment, the sensor unit is configured to be located such that the dispensing member moves away from the sensor unit to dispense medicament from the medicament reservoir. This arrangement allows for a thinner medicament delivery device.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying drawings, in which:

FIG. 6A is a perspective view of a button and the number sleeve of the injection device of FIG. 1;

FIG. 6B is another perspective view of the button and number sleeve of the injection device of FIG. 1;

FIG. 7 is a perspective view of parts of the drive mechanism of the injection device of FIG. 1;

FIGS. 12A and 12B depict an interaction between the drive sleeve and number sleeve of the injection device of FIG. 1;

FIG. 13 is a side view of the dosage measurement system of FIG. 1;

DETAILED DESCRIPTION

Figure 1:
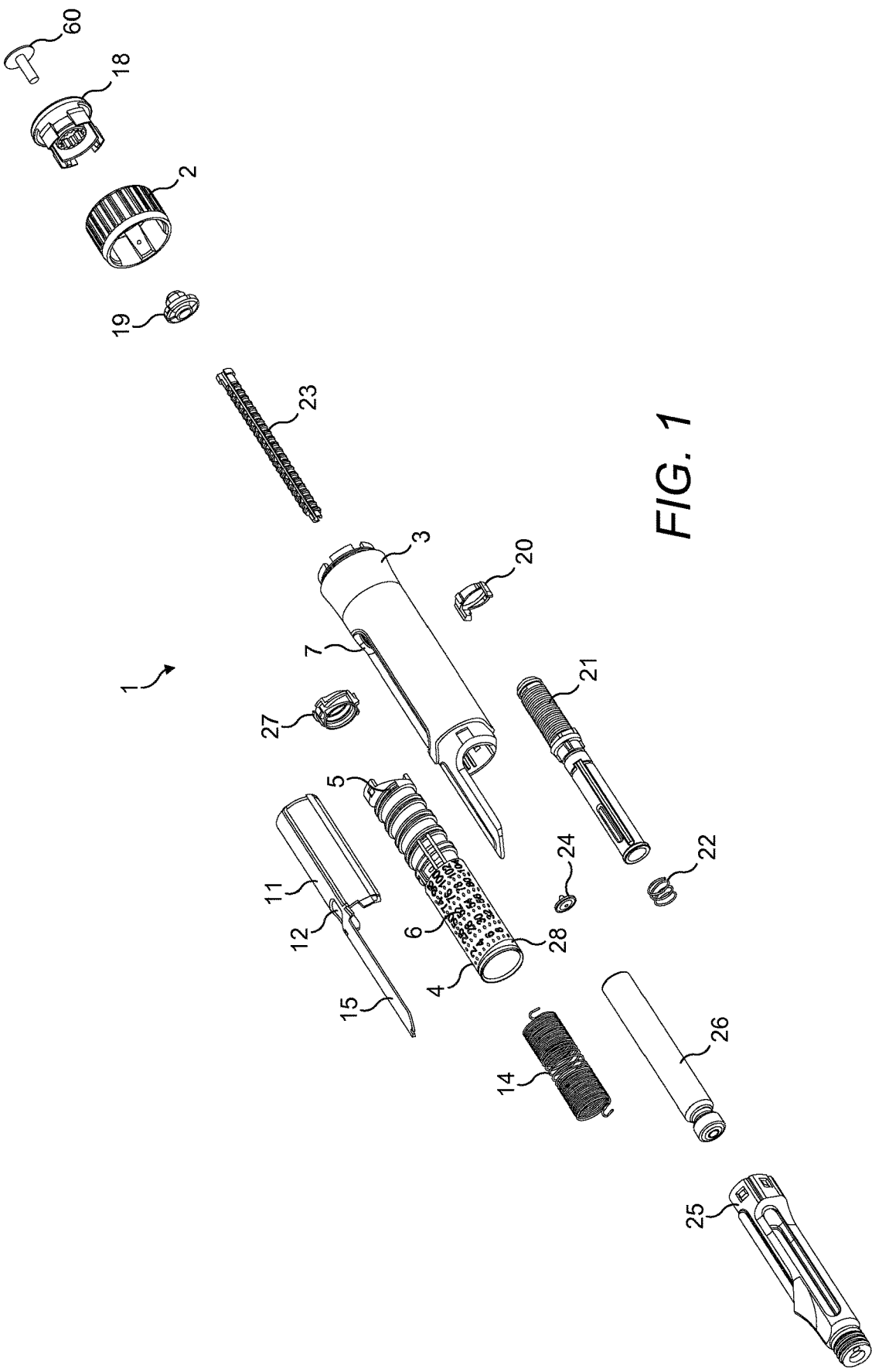
FIG. 1 is an exploded view of a medicament delivery system according to a first embodiment of the disclosure, comprising an injection device and a dosage measurement system.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

The term "distal" refers to a location that is relatively closer to a site of injection, and the term "proximal" refers to a location that is relatively further away from the injection site.

FIG. 1 is an exploded view of the components of a first embodiment of medicament delivery system comprising a medicament delivery device 1 and a dosage measurement system 60.

In the present embodiment, the medicament delivery device 1 is in the form of an injection device 1. The injection device 1 comprises a dose dial 2 in the form of a dial grip 2, a body or housing 3 with an elongated window 7, and a dose scale drum in the form of a number sleeve 4.

The number sleeve 4 has an outer thread 5 on its outer peripheral surface extending in a helical pattern from a distal end to a proximal end. The number sleeve 4 carries indicia 6 which are printed on the number sleeve. The indicia 6 are on the number sleeve 4 in a helical pattern.

The injection device 1 further comprises a sliding element 11 configured as a gauge component with a sliding window 12.

The injection device 1 further comprises a dispensing mechanism comprising a drive spring 14 in the form of a torsion spring 14, a trigger button 18, a clutch plate 19, a last dose nut 20, a drive sleeve 21, a clutch spring 22, a dispensing member in the form of a lead screw 23, and a bearing 24 provided at a distal end of the lead screw 23

A cartridge holder 25 is provided that can be attached to the distal end of the housing 3 and that receives a cartridge 26 which is filled with a medicament and which has a bung (not shown) located inside the cartridge 26. When the bearing 24 is moved in the distal direction, the bearing 24 displaces the bung such that medicament is dispensed from the cartridge 26 when a dispense interface such as a double ended needle cannula is attached to the distal end of the cartridge 26.

The number sleeve 4 comprises an upper number sleeve part 27 referred to a number sleeve upper 27 and a lower number sleeve part 28 referred to as number sleeve lower 28. The dose dial 2 and the button 18 are separate individual components. In the present embodiment, all components are located concentrically about a common principal longitudinal axis of the mechanism. The body or housing 3 may also be a body element that it fixed to an outer housing or casing.

The button 18 is permanently splined to the dose dial 2. It is also splined to the number sleeve upper 28 when the button 18 is not pressed, but this spline interface is disconnected when the button 18 is pressed. When the button 18 is pressed, splines on the button 18 engage with splines on the housing 3 preventing rotation of the button 18 (and hence the dose dial 2) during dispense. These splines disengage when the button 18 is released, allowing a dose to be dialled.

The dose dial 2 is axially constrained to the housing 3. It is rotationally constrained, via the splined interface to the button 18. The number sleeve lower 28 is rigidly fixed to the number sleeve upper 27 during assembly to form the number sleeve 4 and is a separate component to simplify number sleeve 4 mould tooling and assembly. This sub assembly is constrained to the housing 3 by holding elements (not shown) towards the distal end to allow rotation but not translation. The number sleeve lower 28 is marked with indices in the form of a sequence of numbers, which are visible through the window 12 of the sliding element 11 and the window 7 in the housing 3 to denote the dialled dose of medicament.

The clutch plate 19 is splined to the number sleeve 4. It is also coupled to the drive sleeve 21 via a ratchet interface. The ratchet provides a detented position between the number sleeve 4 and the drive sleeve 21 corresponding to each dose unit and engages different ramped tooth angles during clockwise and anti-clockwise relative rotation. The sliding element 11 is constrained to prevent rotation but allow translation relative to the housing 3 via a splined interface. The sliding element 11 has a helical feature on its inner surface which engages with the helical outer thread 5 cut in the number sleeve 4 such that rotation of the number sleeve 4 causes axial translation of the sliding element 11. This helical feature on the sliding element 11 also creates stop abutments against the end of the helical cut in the number sleeve 4 to limit the minimum and maximum dose that can be set.

The last dose nut 20 is located between the number sleeve 4 and the drive sleeve 21. It is rotationally constrained to the number sleeve 4 via a splined interface. It moves along a helical path relative to the drive sleeve 21 via a threaded interface when relative rotation occurs between the number sleeve 4 and drive sleeve 21. The drive sleeve 21 extends from the interface with the clutch plate 19 to the contact with the clutch spring 22. A splined tooth interface with the number sleeve 4 is not engaged during dialling, but engages when the button 18 is pressed, preventing relative rotation between the drive sleeve 21 and number sleeve 4 during dispense.

A further splined tooth interface with the housing 3 prevents rotation of the drive sleeve 21 during dose setting. When the button 18 is pressed, the drive sleeve 21 and the housing 3 disengage allowing the drive sleeve 21 to rotate. The helical drive spring 14 is charged and stores energy during dose setting by the action of the user rotating the dose dial 2. The spring energy is stored until the mechanism is triggered for dispense at which point the energy stored is used to deliver the medicament from the cartridge to the user. The drive spring 14 is attached at one end to the housing 3 and at the other end to the number sleeve 4. The drive spring 14 is pre-wound upon assembly, such that it applies a torque to the number sleeve 4 when the mechanism is at zero units dialled. The action of rotating the dose dial 2 to set a dose rotates the number sleeve 4 relative to the housing 3 and charges the drive spring 14 further.

The lead screw 23 is rotationally constrained to the drive sleeve 21 via a splined interface. When rotated, the lead screw 23 is forced to move axially relative to the drive sleeve 21, through a threaded interface (not shown) with the housing 3. The bearing 24 is axially constrained to the lead screw 23 and acts on the bung within the liquid medicament cartridge 26.

The axial position of the drive sleeve 21, clutch plate 19 and button 18 is defined by the action of the clutch spring 22, which applies a force on the drive sleeve 21 in the proximal direction. This spring force is reacted via the drive sleeve 21, clutch plate 19 and button 18, and when 'at rest' it is further reacted through the dose dial 2 to the housing 3. The spring force ensures that the ratchet interface is always engaged. In the 'at rest' position, it also ensures that the button splines are engaged with the number sleeve 4 and that the drive sleeve teeth are engaged with the housing 3. The housing 3 provides location for the liquid medication cartridge 26 and cartridge holder 25, windows for viewing the dose number and the sliding element, and a feature on its external surface to axially retain the dose dial 2 (not shown). A removable cap fits over the cartridge holder 25 and is retained via clip features on the housing 3.

Figure 2:
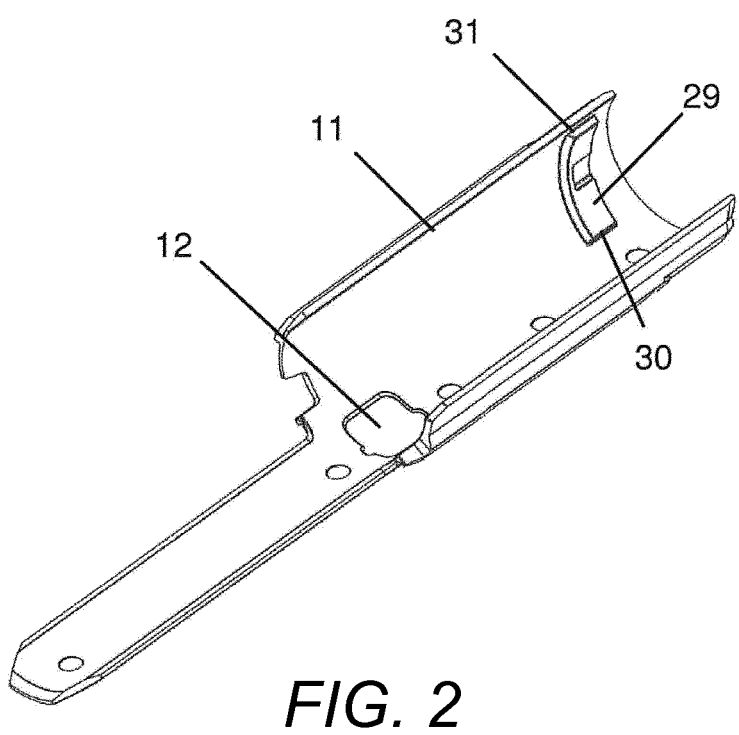
FIG. 2 is a perspective view of a sliding element of the injection device of FIG. 1.
Figure 3:
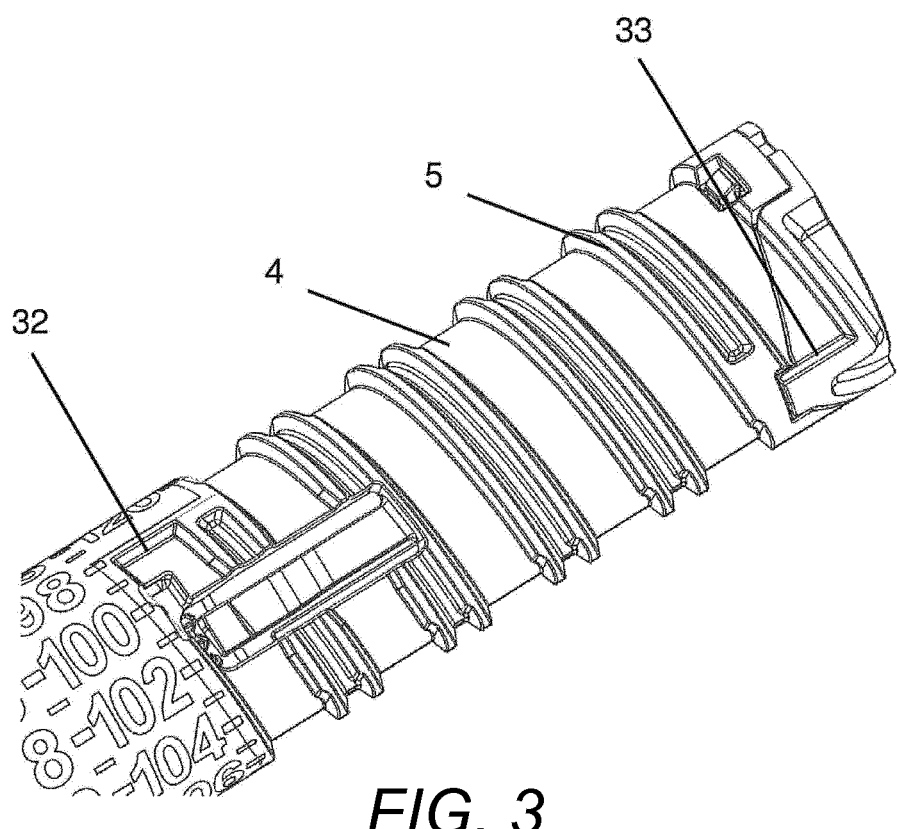
FIG. 3 is a perspective view of a number sleeve of the injection device of FIG. 1.

FIG. 2 shows the inside of the sliding element 11 with the window 12 and a male thread feature 29 on the inner surface of the sliding element 11 that engages the outer thread 5 on the number sleeve 4 (see FIG. 3). The thread feature 29 has a zero dose abutment 30 and a maximum dose abutment 31. As shown in FIG. 3, the outer thread 5 has a zero dose abutment 32 at one end of the thread 5 and a maximum dose abutment 33 at the other end of the outer thread 5 so that any dose size can be selected between zero and a pre-defined maximum, in increments to suit the medicament and user profile. The drive spring 14, which has a number of pre-wound turns applied to it during assembly of the device, applies a torque to the number sleeve 4 and is prevented from rotating by the zero dose abutment.

Figure 4:
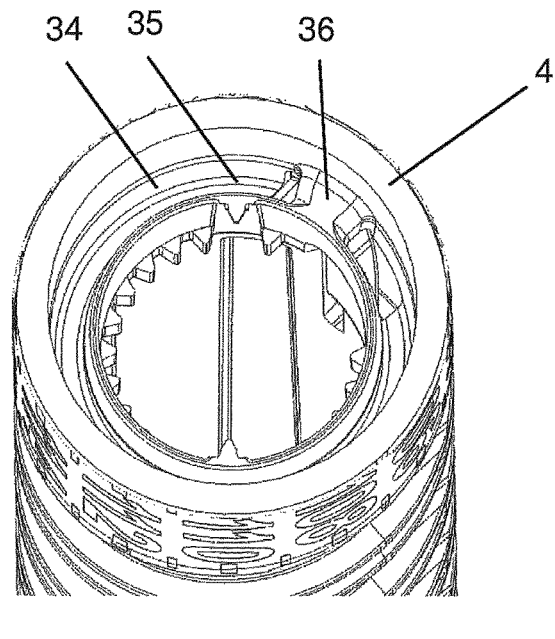
FIG. 4 is a perspective view of another section of the number sleeve of FIG. 3.

As shown in FIG. 4, the inner surface of the number sleeve 4 has a lead-in 34 followed by a groove 35 and an anchor point 36. Automated assembly of the drive spring 14 into the number sleeve may be achieved by incorporating the large lead-in 34 and the groove feature 35. As the drive spring 14 is rotated during assembly, a hook end 37 at the one end of the drive spring 14 (see FIG. 5) locates in the groove feature 35 before engaging the anchor point 36 in the number sleeve 4.

Figure 5:
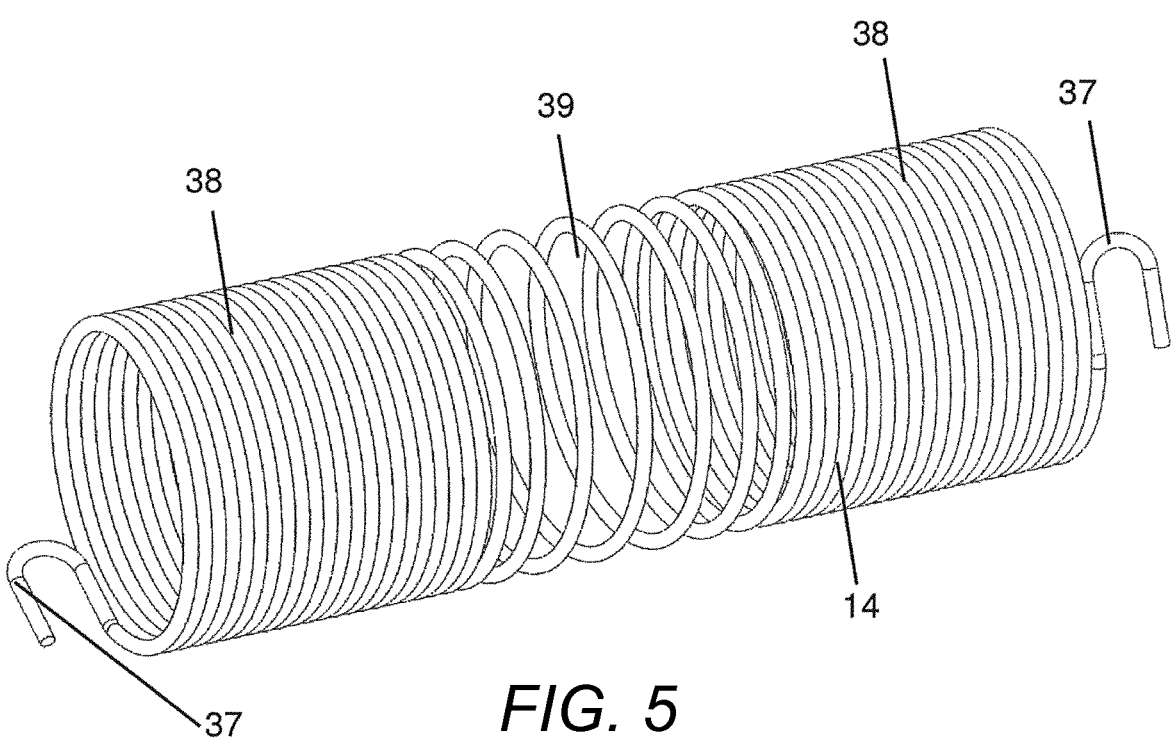
FIG. 5 is a perspective view of a drive spring of the injection device of FIG. 1.

As shown in FIG. 5, the drive spring 14 is formed from a helical wire with at least two different pitches. Both ends are formed from 'closed' coils 38, i.e. the pitch equals the wire diameter and each coil contacts the adjacent coil. The central portion has 'open' coils 39, i.e. the coils do not contact each other. Following assembly, compression in the drive spring 14 biases the number sleeve 5 axially relative to the housing 3 in a consistent direction, reducing the effects of geometric tolerances.

For selecting a dose, the user rotates the dial grip 2 clockwise. As shown in FIGS. 6A and 6B, the button 18 has inner splines 40 for engaging corresponding splines 41 on the upper part of number sleeve 4 to create a splined interface 40/41. The dial grip 2 is splined to the button 18, wherein the button 18 has a further set of splines 42 for engagement with corresponding splines of the housing 3. During dose selection, rotation of the dial grip 2 is transferred to the button 18. The button 18 is in turn splined to the number sleeve upper 27 (during dose selection only) via the splines 40. The number sleeve upper 27 is permanently fixed to the number sleeve lower 28 to form the number sleeve 4. Therefore, rotation of the dial grip 2 generates an identical rotation in the number sleeve 4. Rotation of the number sleeve 4 causes charging of the drive spring 14, increasing the energy stored by the drive spring 14. As the number sleeve 4 rotates, the sliding element 11 translates axially due to its threaded engagement with the number sleeve 4 thereby showing the value of the dialled dose.

As shown in FIG. 7, the drive sleeve 21 has splines 43 for engaging corresponding splines 44 formed on the inside of the housing 3 to create a splined interface 43/44. The drive sleeve 21 is prevented from rotating as the dose is set and the number sleeve 4 is rotated, due to the engagement of its splined teeth 43 with the teeth 44 of the housing 3. Relative rotation therefore occurs between the clutch plate 19 that is driven by the number sleeve 4 and the drive sleeve 21 via the ratchet interface.

Figure 8A:
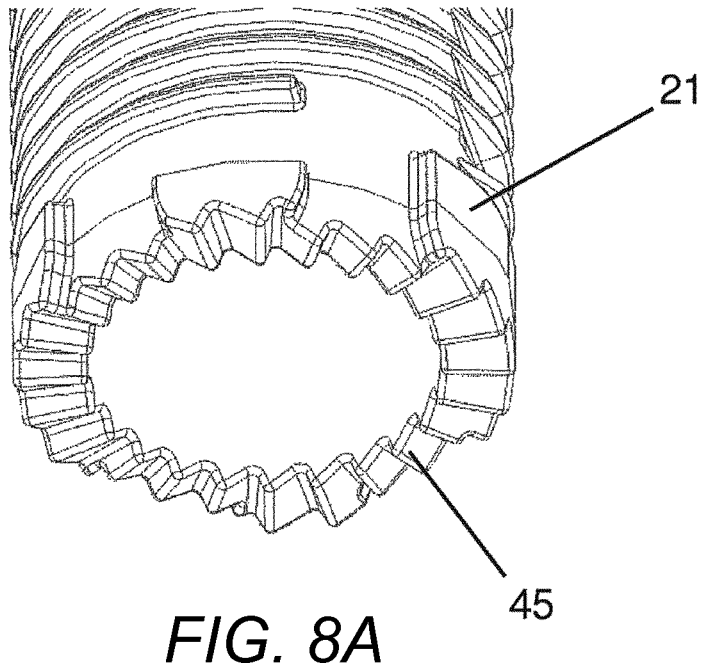
FIG. 8A is a perspective view of a drive sleeve of the injection device of FIG. 1.
Figure 8B:
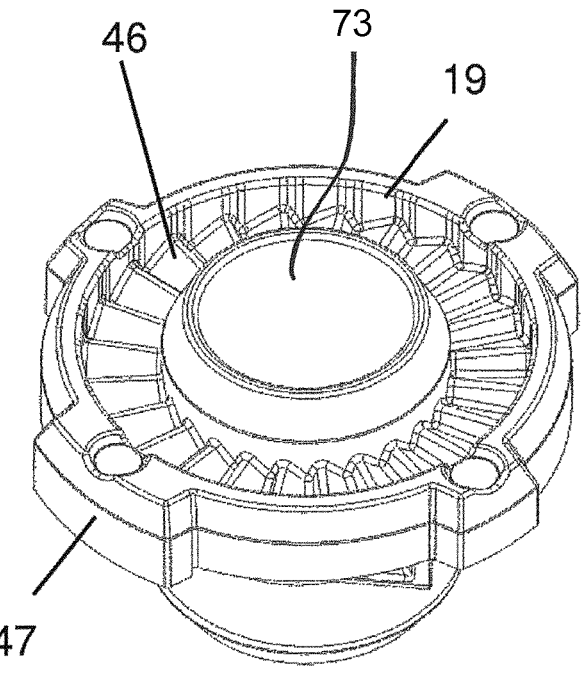
FIG. 8B is a perspective view of a clutch plate of the injection device of FIG. 1.

As shown in FIGS. 8A and 8B, an end surface of the drive sleeve 21 is provided with angled teeth 45 and the clutch plate 19 is provided with angled teeth 46. The angled teeth 45 of the drive sleeve 21 form the ratchet interface 45/46 together with the angled teeth 46 on the clutch plate 19.

On the outer circumference of the clutch plate 19, splined teeth 47 for engaging a corresponding groove on the number sleeve 4 are formed. The user torque required to rotate the dial grip 2 is a sum of the torque required to wind up the drive spring 14, and the torque required to overhaul the ratchet interface 45/46. The clutch spring 22 is designed to provide an axial force to the ratchet interface 45/46 and to bias the clutch plate 19 onto the drive sleeve 21. This axial load acts to maintain the ratchet teeth 45, 46 engagement of the clutch plate 19 and the drive sleeve 21. The torque required to overhaul the ratchet interface 45/46 in the dose set direction is a function of the axial load applied by the clutch spring 22, the clockwise ramp angle of the ratchet, the friction coefficient between the mating surfaces and the mean radius of the ratchet features. As the user rotates the dial grip 2 sufficiently to increment the mechanism by 1 increment, the number sleeve 14 rotates relative to the drive sleeve 21 by 1 ratchet tooth. At this point the ratchet teeth 45, 46 re-engage into the next detented position. An audible click is generated by the ratchet re-engagement, and tactile feedback is given by the change in torque input required.

With no user torque applied to the dial grip 2, the number sleeve 4 is prevented from rotating back under the torque applied by the drive spring 14, solely by the ratchet engagement 45/46 between the clutch plate 19 and the drive sleeve 21. The torque necessary to overhaul the ratchet interface 45/46 in the anti-clockwise direction is a function of the axial load applied by the clutch spring 22, the anti-clockwise ramp angle of the ratchet teeth 45, 46, the friction coefficient between the mating surfaces and the mean radius of the ratchet features. The torque necessary to overhaul the ratchet interface 45/46 must be greater than the torque applied to the number sleeve 4 (and hence clutch plate 19) by the drive spring 14. The ratchet ramp angle is therefore increased in the anticlockwise direction to ensure this is the case whilst ensuring the dial-up torque is as low as possible. The user may choose to increase the selected dose by continuing to rotate the dial grip 2 in the clockwise direction. The process of overhauling the ratchet interfaces 45/46 between the number sleeve 4 and drive sleeve 21 is repeated for each dose increment. Additional energy is stored within the drive spring 14 for each dose increment and audible and tactile feedback is provided for each increment dialled by the re-engagement of the ratchet teeth 45, 46. The torque required to rotate the dial grip 2 increases as the torque required to wind up the drive spring 14 increases. The torque required to overhaul the ratchet interface 45/46 in the anti-clockwise direction must therefore be greater than the torque applied to the number sleeve 4 by the drive spring 14 when the maximum dose has been reached.

If the user continues to increase the selected dose until the maximum dose limit is reached, the number sleeve 4 engages with the maximum dose abutment 31 on the sliding element 11 (see FIGS. 2 and 3. This prevents further rotation of the number sleeve 4, clutch plate 19 and dial grip 2.

The last dose nut 20 is splined to the number sleeve 4 while the last dose nut 20 is threaded to the drive sleeve 21 such that relative rotation of the number sleeve 4 and the drive sleeve 21 during dose setting also causes the last dose nut 20 to travel along its threaded path towards a last dose abutment on the drive sleeve 21. Depending on how many increments have already been delivered by the mechanism, during selection of a dose, the last dose nut 21 may contact its last dose abutment with the drive sleeve 21. The abutment prevents further relative rotation between the number sleeve 4 and the drive sleeve 21 and therefore limits the dose that can be selected. The position of the last dose nut 20 is determined by the total number of relative rotations between the number sleeve 4 and the drive sleeve 21, which have occurred each time the user sets a dose.

When a dose has been set, the user is able to deselect any number of increments from this dose. Deselecting a dose is achieved by the user rotating the dial grip 2 anti-clockwise. The torque applied to the dial grip 2 by the user is sufficient, when combined with the torque applied by the drive spring 14, to overhaul the ratchet interface 45/46 between the clutch plate 19 and the drive sleeve 21 in the anti-clockwise direction. When the ratchet interface 45/46 is overhauled, anti-clockwise rotation occurs in the number sleeve 4 (via the clutch plate 19), which returns the number sleeve 4 towards the zero dose position, and unwinds the drive spring 14. The relative rotation between the number sleeve 4 and drive sleeve 21 causes the last dose nut 20 to return along its helical path, away from the last dose abutment.

Figure 9A:
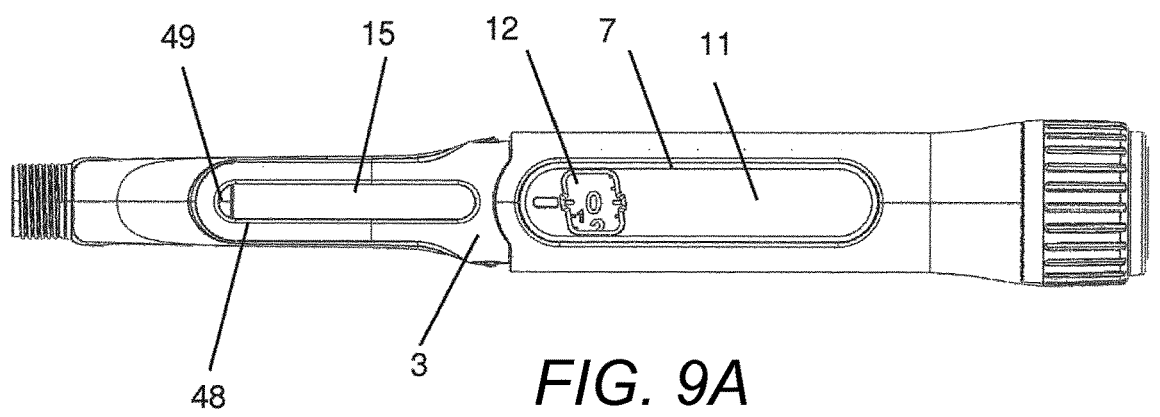
FIGS. 9A and 9B depict a dose setting sequence of the injection device of FIG. 1 in a side view.
Figure 9B:
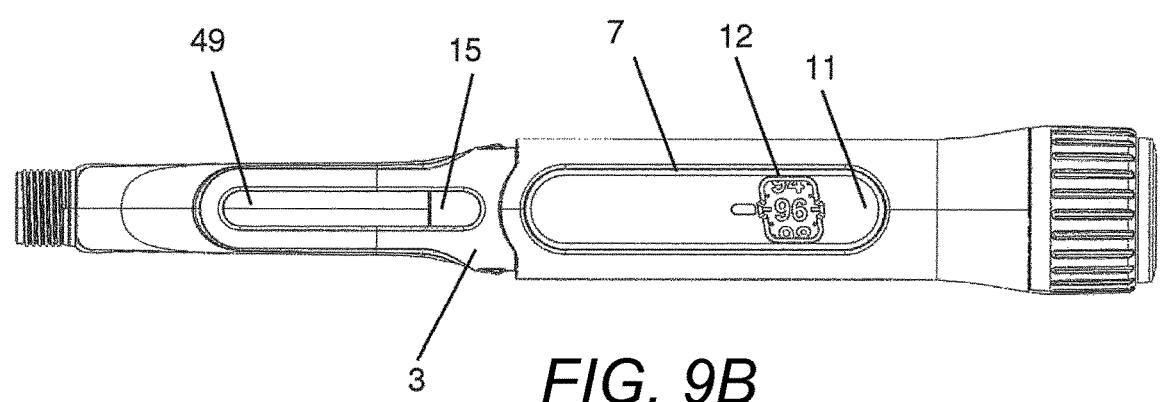

As shown in FIGS. 9A and 9B, the sliding element 11 has flanges or extensions on either side of the window area which cover the numbers printed on the number sleeve 4 adjacent to the dialled dose to ensure only the set dose number is made visible to the user. The injection device 1 includes a visual feedback feature in addition to the discrete dose number display. The distal end of the sliding element

11 has the extension 15 (see FIG. 1) that creates a sliding scale through a window 48 in the housing 3. Window 48 may be smaller than window 7.

As a dose is set by the user, the sliding element 11 translates axially, the distance moved proportional to the magnitude of the dose set. This feature gives clear feedback to the user regarding the approximate size of the dose set. The dispense speed of the injection device 1 may be higher than for a manual injector device, so it may not be possible to read the numerical dose display during dispense. The sliding element 11 provides feedback to the user during dispense regarding dispense progress without the need to read the dose number itself.

The window 48 may be formed by an opaque element on the sliding element 11 revealing a contrasting coloured component 49 underneath. Alternatively, a revealable element 49 may be printed with coarse dose numbers or other indices to provide more precise resolution. In addition, this display simulates a syringe action during dose set and dispense.

To reduce dust ingress and prevent the user from touching moving parts, the viewing openings 7 and 48 in the housing 3 are covered by translucent windows. These windows 7, 48 may be separate components, but in this embodiment they are incorporated into the housing 3 using 'twin-shot' moulding technology. A first shot of translucent material forms the internal features and the windows, and then a 'second shot' of opaque material forms the outer cover of the housing 3.

Delivery of a dose is initiated by the user depressing the button 18 axially. When the button 18 (see FIGS. 6A and 6B) is depressed, the splines 40 and 41 between the button 18 and the number sleeve 4 disengage, rotationally disconnecting the button 18 and dial grip 21 from the delivery mechanism.

Figure 10:
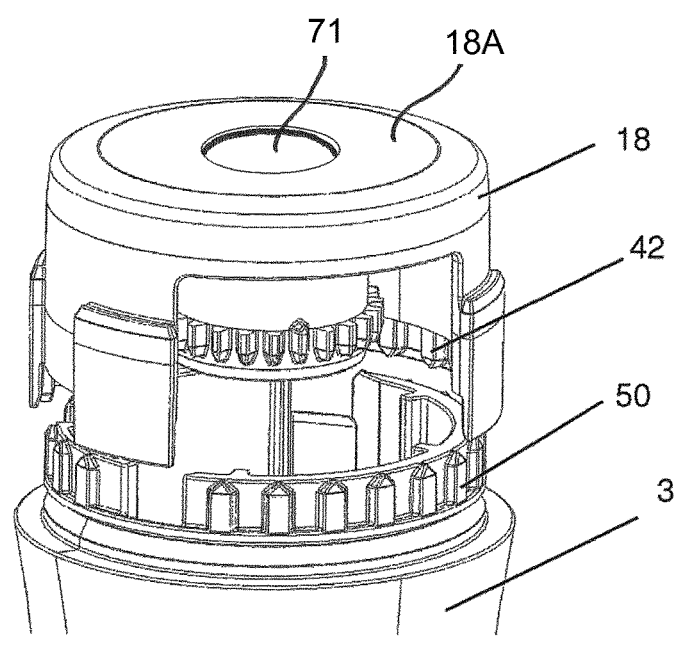
FIG. 10 is a perspective view of the button and a housing of the injection device of FIG. 1.

As shown in FIG. 10, the splines 42 on the button 18 engage with splines 50 on the housing 3 preventing rotation of the button 18 (and hence the dial grip 21) during dispense. As the button 18 is stationary during dispense, it can be used in a dispense clicker mechanism. A stop feature in the housing 3 limits axial travel of the button 18 and reacts any axial abuse loads applied by the user, reducing the risk of damaging internal components.

Figure 11A:
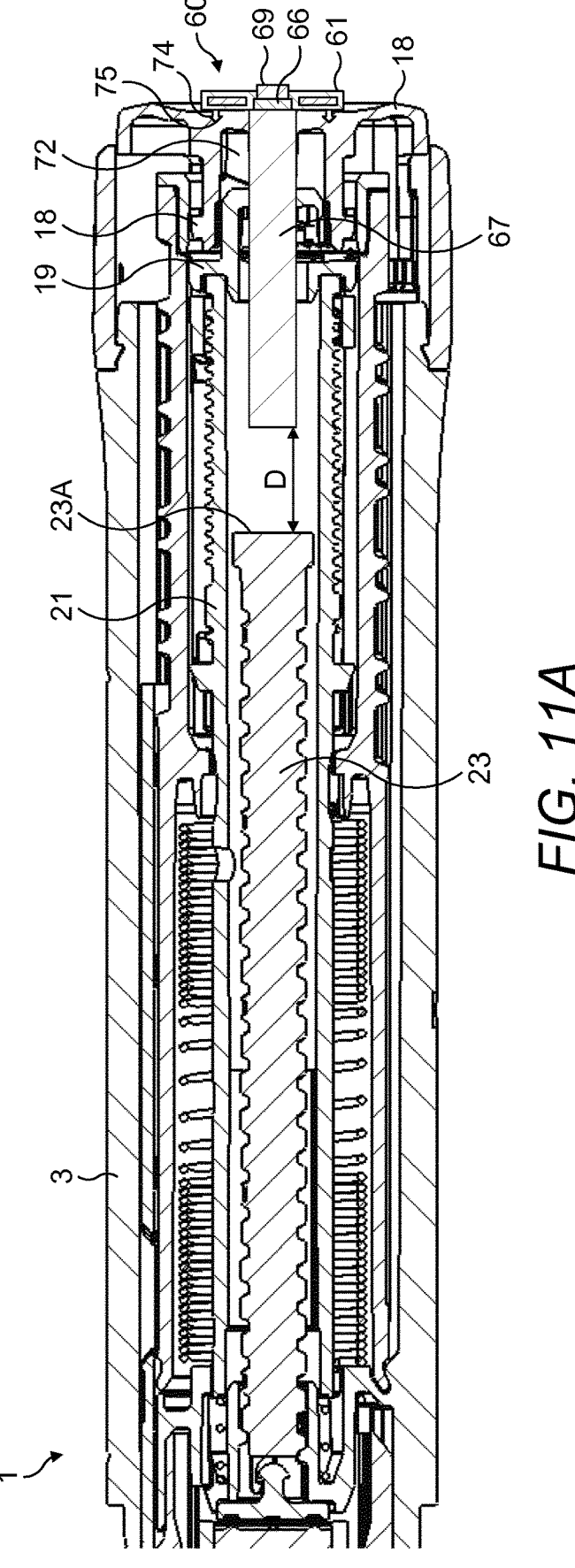
FIG. 11A is a cross-sectional side view of a rear part of the medicament delivery system of FIG. 1.

As shown in FIG. 11A, the clutch plate 19, arranged between the drive sleeve 21 and the button 18, is moved axially by the button 18. Moreover, the drive sleeve 21 is moved axially by the clutch plate 19. As shown in FIGS. 12A and 12B, the axial displacement of the drive sleeve 21 engages splines 51 on the drive sleeve 21 with splines 52 on the number sleeve 4 so that a splined tooth interface 51/52 is formed preventing relative rotation between the drive sleeve 21 and number sleeve 4 during dispense.

The splined tooth interface 43/44 (shown in FIG. 7) between the drive sleeve 21 and the housing 3 disengages, so that the drive sleeve 21 can now rotate relative to the housing 3 and is driven by the drive spring 14 via the number sleeve 4, and clutch plate 19. Rotation of the drive sleeve 21 causes the lead screw 23 to rotate due to their splined engagement, and the lead screw 23 then advances due to its threaded engagement to the housing 3. The number sleeve 4 rotation also causes the sliding element 11 to traverse axially back to its zero position whereby the zero dose abutment (shown in FIGS. 2 and 3) stops the mechanism.

It is possible to angle the spline teeth on either the drive sleeve 21 or the housing 3 so that when the zero dose abutment 30 stops rotation of the number sleeve 4 and hence the drive sleeve 21 at the end of the dose and the button 18 is released, the spline teeth between the drive sleeve 21 and the housing 3 rotate the drive sleeve 21 backwards by a small amount. This moves the lead screw 23 axially back away from the bung and rotates the number sleeve lower 28 from the zero dose stop position, helping to prevent possible weepage.

In the present embodiment, the dosage measurement system 60 is in the form of a dosage measurement device 60 that is attached to a proximal end of the injection device 1.

The dosage measurement device 60 comprises a housing 61 and a display 62 for presenting dosage information. However, it should be recognised that in alternative embodiments (not shown) the display 62 is omitted.

Figure 14:
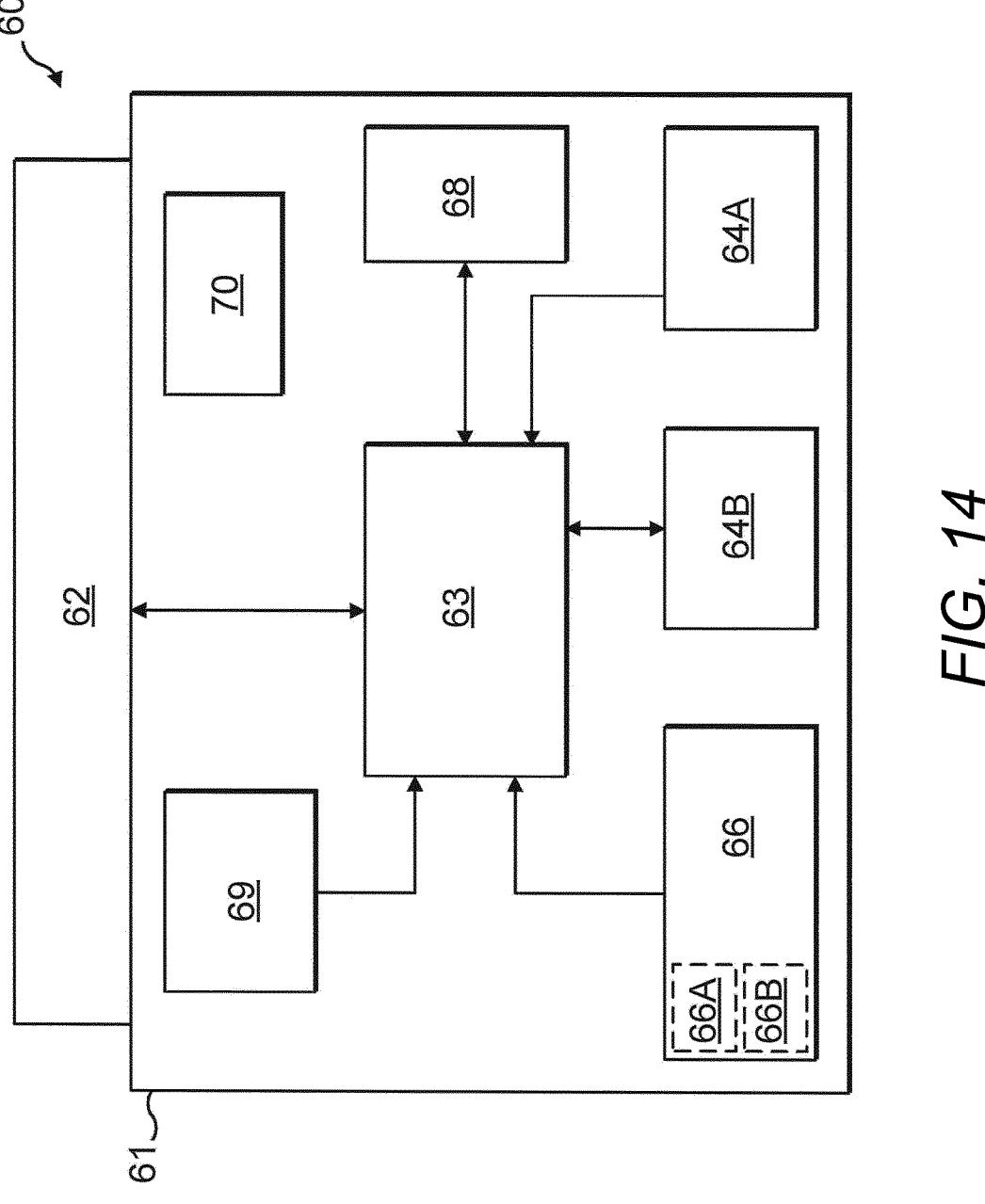
FIG. 14 is a block diagram of the dosage measurement system of FIG. 1.

As shown in FIG. 14, the data measurement device 60 also includes one or more processors 63, such as a microprocessor, a Digital Signal Processor (DSP), Application Specific Integrated Circuit (ASIC), Field Programmable Gate Array (FPGA) or the like, together with one or more computer readable memory media 64. In the present embodiment, the computer readable memory media 64 comprises memory units 64A, 64B, including program memory 64A and main memory 64B, which can store software for execution by the processor 63.

A sensor unit 65, comprising one or more sensors 66, is provided. The sensor unit 65 is configured to detect movement of a dispensing member of the dispensing mechanism, which in the present example is a lead screw 23. In this particular embodiment, the sensor 66 comprises an optical sensor 66. The optical sensor 66 includes a light source 66A, such as a laser, and a light detector 66B, such as an optical transducer.

The sensor unit 65 further comprises a light guide 67, which is described in more detail below.

The dosage measurement device 60 further comprises an output 68, a power switch 69 and a battery 70. Actuation of the power switch 69 powers the dosage measurement device 60 on and off.

In one embodiment, the power switch 69 comprises a button 69 on the housing 61 of the dosage measurement device 60 that is actuated by the user. In another embodiment, the power switch 69 is configured to respond to pressure applied to the display 62 by powering the dosage measurement device 60 on or off. In yet another embodiment (not shown), the power switch 69 is actuated when the user actuates the button 18. For instance, the power switch 69 may comprise an electrical contact (not shown) on the button 18 that makes electrical contact with a second electrical contact (not shown) on a different part of the injection device 1, for example, the housing 3 or number sleeve 4, when the button 18 is pressed to power the dosage measurement device 60 on. When the first and second electrical contacts make contact, a power circuit may be closed such that the dosage measurement device 60 is powered on.

Advantageously, such an arrangement helps to ensure that the dosage measurement device 60 is only operated to measure a dosage being delivered when the button 18 is pressed into the housing 3 and is thus in its operating position. This may improve accuracy of dosage measurement because otherwise movement of the button 18 axially into the housing 3, which moves the sensor unit 65 towards the lead screw 23 and thus reduces the distance (depicted by arrow 'D' in FIGS. 11A and 11B) therebetween, may appear to the sensor unit 65 as if the medicament reservoir is being refilled with medicament. Moreover, movement of the button 18 axially out of the housing 3 when the button 18 is released, which moves the sensor unit 65 away the lead screw 23 and thus increases the distance 'D' therebetween, may appear to the sensor unit 65 as if a dosage is being expelled from the injection device 1. However, it should be recognised that other arrangements to help ensure that the dosage measurement device 60 is only operated to measure a dosage being delivered when the button 18 is in its operating position are also possible. For instance, the processor 63 may be configured to only start measuring the dosage dispensed from the injection device 1 once it has calculated that the sensor unit 65 has moved towards the lead screw 23 by a distance D that corresponds to the button 18 being actuated by the user. Additionally, or alternatively, if the processor 63 calculates that the sensor unit 65 has moved relative to the lead screw 23 by a distance D in a time period that is consistent with the button 18 being released, the processor 63 may disregard this dosage measurement or flag it as the button 18 being released. In a yet further embodiment, the power switch 69 is arranged such that pressing the button 18 results in the power switch 69 simultaneously being pressed to power on the dosage measurement device 60 and/or releasing the button 18 results in the power switch 69 being released to power off the dosage measurement device 60. In another embodiment, instead of being a power switch 69 that powers the dosage measurement device on and off, the switch 69 may be pressed to run a particular program or routine, for example, to cause the processor 63 to run a dosage determining program.

In the present embodiment, the processor 63, computer readable memory media 64, sensor 66, output 68 and battery 70 are located within the housing 61. However, it should be recognised that in alternative embodiments (not shown) one or more of these components may be located external of the housing 61.

The output 68 may be a wireless communications interface for communicating with another device via a wireless network such as wi-fi or Bluetooth®, or an interface for a wired communications link, such as a socket for receiving a Universal Series Bus (USB), mini-USB or micro-USB connector.

Figure 11B:
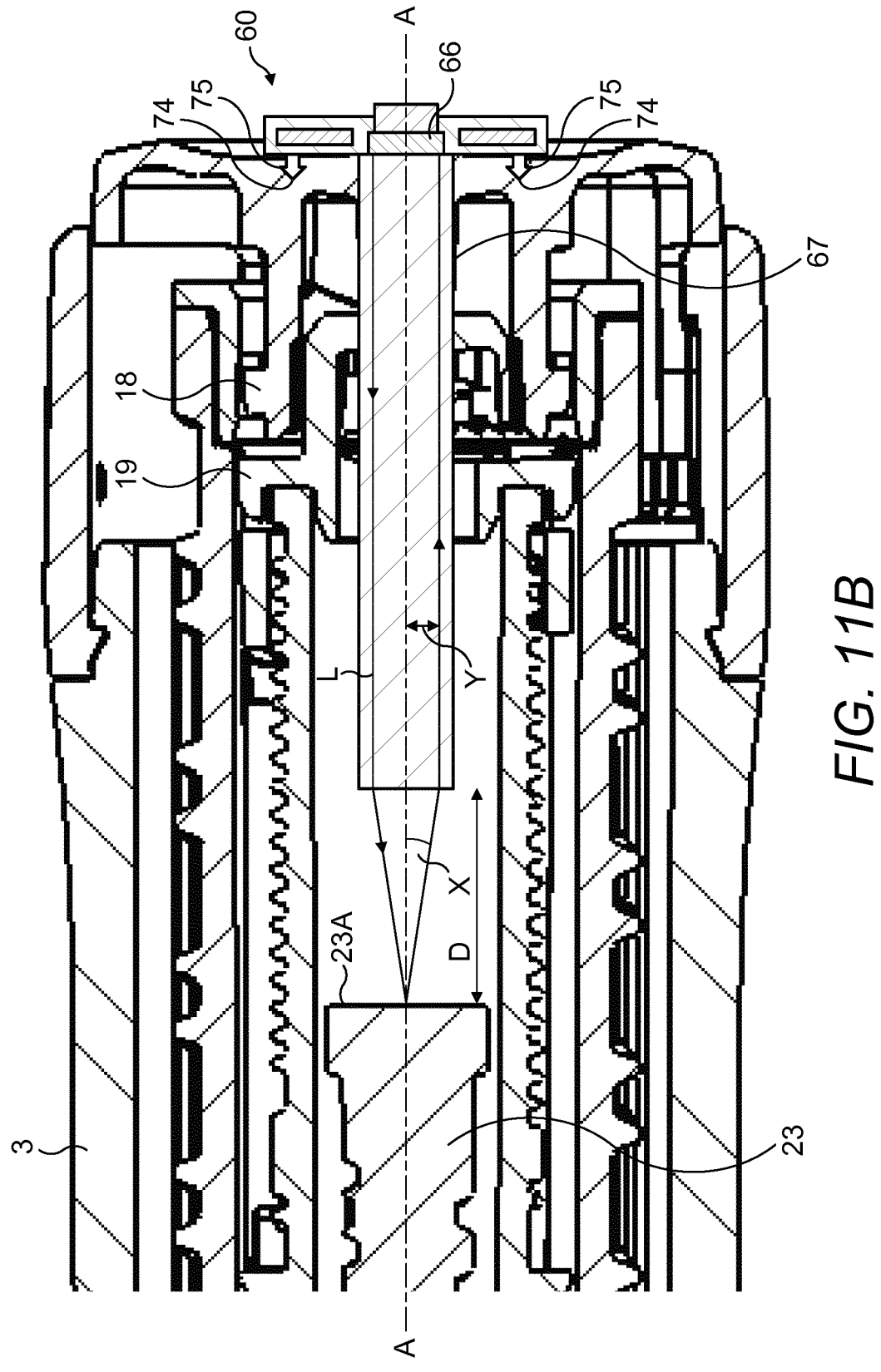
FIG. 11B is a close-up cross-sectional side view of the rear part of the medicament delivery system of FIG. 11A

FIGS. 11A and 11B show the dosage measurement device 60 and the proximal end of the injection device 1.

The button 18 includes an aperture 71 in its proximal surface 18A, configured such that at least a portion of the dosage measurement device 60 can be received in a space 72 within the button 18. In the present embodiment, the clutch plate 19 comprises an aperture 73 and at least a portion of the data measurement device 60 extends through the aperture 73 in the clutch plate 19 to be received in the proximal end of the drive sleeve 21. In more detail, the prism 67 extends axially from the housing 61 of the dosage measurement device 60 such that the prism 67 extends through the space 72 of the button 18 and through the aperture 73 of the clutch plate 19. An end 67A of the prism 67 is received in the hollow centre of the drive sleeve 21.

The housing 61 of the dosage measurement device 60 comprises one or more attachment formations 74 that are configured to engage with corresponding attachment formations 75 on the button 18. In the present embodiment, the attachment formations 74 of the dosage measurement device 60 comprise projections 74 that engage with respective recesses 75 in the button 18 such that the dosage measurement device 60 can be clipped to the button 18.

However, it should be recognised that in alternative embodiments (not shown) the attachment formations 74 are provided on a different component of the injection device 1.

In some embodiments, the engagement of the attachment formations 74, 75 is such that the dosage measurement device 60 cannot rotate relative to the button 18 when attached thereto.

In embodiments wherein the dosage measurement device 60 is to be releasably attachable to the injection device 1, the attachment formations 74, 75 may provide a clip-type arrangement that allows for easy removal of the dosage measurement device 60. Such an arrangement may be useful where the dosage measurement device 60 is to be used with disposable injection devices 1, since it allows the dosage measurement device 60 to be removed from an injection device 1 and reused. A removable dosage measurement device 60 also affords the user greater flexibility since the user is able to attach and remove the dosage measurement device 60 at will.

In some embodiments, the attachment formations 74, 75 may be configured to permanently attach the dosage measurement device 60 to the injection device 1, for example, using a "snap-fit". Alternatively, the dosage measurement device 60 may be permanently attached in other ways, for example, through bonding. Such permanent attachment may be useful where the injection device 1 is reusable. The number and/or positions of the attachment formations 74, 75 may be configured so that the dosage measurement device 60 can only be attached to the injection device 1 in one particular orientation relative to the injection device 1.

The light guide 67 is configured such that, when the dosage measurement device 60 is attached to the injection device 1, light emitted from the light source 66A is transmitted axially along the length of the light guide 67 and is then transmitted from the end 67A of the light guide 67 and directed towards a proximal-facing end surface 23A of the lead screw 23. The light (depicted by arrow I' in FIG. 11B) is reflected from the end surface 23A of the lead screw 23 and travels back towards the light guide 67 wherein the light enters the light guide 67 and is transmitted through the light guide 67. Thus, the reflected light travels through the light guide 67 until it reaches the sensor 66, wherein the light is detected by the light detector 66B.

The light may travel generally in the axial direction between the light guide 67 and the end surface 23A of the lead screw 23. In the present example, the light is transmitted from the light guide 67 at an angle relative to an axis A-A, which in the present embodiment is the central axis A-A of the injection device 1 but in alternative embodiments may be an axis parallel to the central axis A-A of have a different orientation, such that when the light impinges on the end surface 23A of the lead screw 23 the light is reflected from the end surface 23A at an angle X relative to the central axis A-A. The light then travels back towards the light guide 67 at said angle X relative to the central axis A-A and is then transmitted through the light guide 67 in the axial direction until the light reaches the sensor 66. To facilitate this, the end 67A of the light guide 67 may comprise a prism 67A. The prism 67A ensures that the light is transmitted from the light guide 67 at an angle relative to the central axis A-A.

The distance Y between the reflected beam of light L and the central axis A-A when the light enters the end 67A of the light guide 67 depends on the distance D between the end 67A of the light guide 67 and the end surface 23A of the lead screw 63. The optical sensor 66 is configured to detect the distance Y. For example, the light detector 66B may comprise an array of light detection sensors (not shown), wherein a different light detection sensor of the array detects the reflected beam for different values of distance Y. The array of light detection sensors may be arranged in an array radially.

In certain embodiments, the sensor 66 may be arranged to emit and/or detect only light with a particular frequency or particular polarisation characteristics, in order to mitigate effects of stray light. The sensor 66 may be configured to emit and/or detect a laser beam.

During the delivery of the medicament, the drive sleeve 21 rotates to rotate the lead screw 23. This causes the lead screw 23 to move axially in the distal direction relative to the housing 3 due to threaded engagement with the housing 3 or another component of the injection device 1. Thus, the end surface 23A of the lead screw 23 moves axially away from the sensor unit 65 such that the distance D therebetween increases. The increase in the distance D between the sensor unit 65 and the end surface 23A of the lead screw 23 causes the distance Y between the central axis A-A and the point that the reflected beam of light L enters the light guide 67 increases. This increase in distance Y is detected by the light detector 66B. Since the sensor unit 66 is connected to the processor 63, the processor 63 can detect the increase in distance Y and thus determine an amount of medication delivered by the injection device.

When the medicament delivery is complete, the lead screw 23 will cease to move axially relative to the dosage measurement device 60 such that distance D, and thus distance Y, will remain constant. Therefore, the signal from the sensor 66 will stay at a substantially constant level.

In some embodiments, the processor 63 is arranged to monitor the time period that has elapsed from the last change in the output of the sensor 66. When the elapsed time period reaches a predetermined threshold, the medicament delivery is considered to have been completed and the processor 63 proceeds with determining the medicament dose delivered to the user, based on the change in the distance Y that is measured.

The processor 63 then stores the determined medicament dose in the main memory 64B. The processor 63 may also store time stamp information, to provide a log recording delivery of medicament to the user. The processor 63 may then power down the dosage measurement device 60, in order to conserve battery power. Alternatively, the dosage measurement device 60 may be powered off when, or shortly after, the user releases button 18 and/or button 69.

When the dosage measurement device 60 is powered on again, by a user activating the power switch 69, the processor 63 may control the display 62 to show the determined medicament dose information, to aid the memory of the user. Optionally, the processor 63 may monitor an elapsed time since the determined medicament dose was delivered and control the display to show that elapsed time information too. For example, the processor 63 may cause the display 62 to switch periodically between displaying the determined medicament dosage information and the elapsed time.

In some embodiments, the processor 63 is configured to calculate the axial displacement of the lead screw 23 relative to the drive sleeve 21 by calculating the difference between the distance D between the sensor unit 65 and the end surface 23A at the start of medicament delivery and the distance D at the end of medicament delivery. The processor 63 may determine the dosage delivered based on said difference between the distance D at the start and end of the medicament delivery.

The processor 63 may also transmit the determined medicament dosage and, where determined, the time stamp information to another device, such as a computer (not shown). As noted above, the output 68 may be configured to transmit the information using a wireless communications link. Alternatively, the dosage measurement device 60 may be connected to the computer (not shown) using a wired connection (not shown) to allow the information to be uploaded to the computer. The processor 63 may be configured to transmit the information to the computer periodically. In some embodiments, the display 62 may be omitted. In some embodiments, the dosage measurement system 60 may be used to monitor compliance with a particular dosage regime.

The specific embodiments described in detail above are intended merely as examples of how the present disclosure may be implemented. Many variations in the configuration of the dosage measurement device 60 and/or the injection device 1 may be conceived. For example, in an alternative embodiment (not shown) the sensor 66 instead detects a time delay between a light pulse being emitted by the light source 66A and received by the light detector 66B to determine the distance D between the sensor unit 65 and the end surface 23A of the lead screw 23. The larger the distance D, the greater the time delay between the light pulse being emitted and the reflected pulse being received by the sensor 66. Thus, the processor 63 can determine the dosage delivered based on the delay between one or more pulses of light being received. It should be recognised that in some embodiments, the light guide 67 and/or prism 67A may be omitted. In some embodiments, the sensor 66 comprises an optical triangulation sensor configured to measure the distance between the sensor and the end surface 23A of the lead screw 23, and may comprise a laser triangulation sensor.

The dosage measurement system allows for a dosage dispensed from the medicament reservoir to be determined without measuring rotation of a component of the dispensing mechanism. Thus, the sensor unit does not need to have a particular rotational orientation relative to the dispensing member, and does not need to be rotationally fixed relative to the dispensing member during use.

Figure 15:
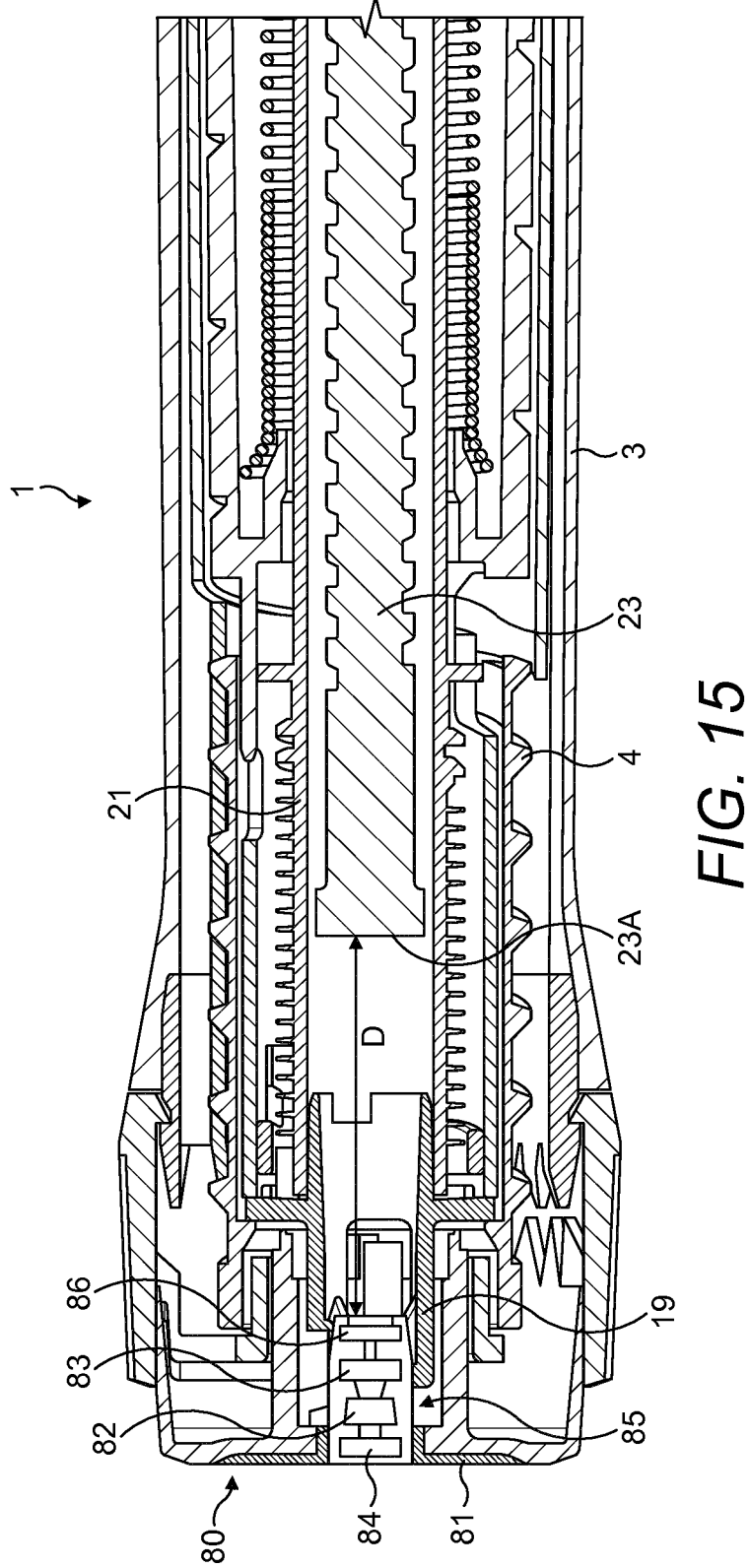
FIG. 15 is a cross-sectional side view of part of a medicament delivery system according to a second embodiment of the disclosure.

Referring now to FIG. 15, a medicament delivery system according to a second embodiment of the disclosure is shown. The medicament delivery system is similar to the measurement delivery system described above in reference to the first embodiment of the disclosure, with like features retaining the same reference numerals. The medicament delivery system comprises a medicament delivery device 1 and a dosage measurement system 80.

The medicament delivery device 1 is in the form of an injection device 1. The dosage measurement system 80 comprises a dosage measurement device 80 that is attached to a proximal end of the injection device 1. The dosage measurement device 80 comprises a housing 81, a battery 82, a processor 83, computer readable memory media (not shown), a power switch (not shown), an output (not shown), and a user interface 84.

A difference between the dosage measurement system 60 of the first embodiment and the dosage measurement system 80 of the second embodiment is that the sensor unit 65 is omitted and is replaced by an alternative sensor unit 85. The sensor unit 85 comprises a sensor 86, which in the present embodiment is an acoustic sensor 86 having an acoustic source (not shown), for example, a speaker, and an acoustic detector (not shown), for example, a microphone. In one embodiment, the acoustic sensor 86 is an ultrasound sensor.

The sensor unit 85 is arranged such that an acoustic signal emitted by the acoustic sensor 86 travels towards the end surface 23A of the lead screw 23 and is reflected back towards the acoustic sensor 86 such that the reflected signal is detected by the acoustic sensor 86. The acoustic sensor 86 is connected to the processor 83.

The processor 83 is configured to determine a dosage dispensed from the injection device 1 based on a characteristic of the reflected signal detected by the acoustic sensor 86, wherein the characteristic of the signal is dependent on the distance D between the sensor unit 85 and the end surface 23A of the lead screw 23. For example, the processor 83 may be configured to determine the dosage dispensed from the injection device 1 based on a detected time delay between a pulse or time varying signal being emitted by the acoustic sensor 86, and the reflected signal being received by the acoustic sensor 86. The larger the distance D between the sensor unit 85 and the end surface 23A of the lead screw 23, the greater the time delay between the signal being transmitted and received. Thus, the processor 83 can determine the dosage delivered based on the delay between one or more signals being transmitted and received. Alternatively, or additionally, the processor 83 may be configured to determine the dosage dispensed from the injection device 1 based on a detected attenuation of the reflected signal received by the acoustic sensor 86, which is the difference in amplitude between the transmitted signal and received signal. The larger the distance D between the sensor unit 85 and the end surface 23A of the lead screw 23, the greater the attenuation of the signal.

The processor 83 may be configured to operate the user interface 84 when a dosage condition is fulfilled, for example, when a predetermined dosage of medicament has been delivered by the injection device 1. The user interface 84 may comprise, for example, a buzzer and/or light.

Figure 16:
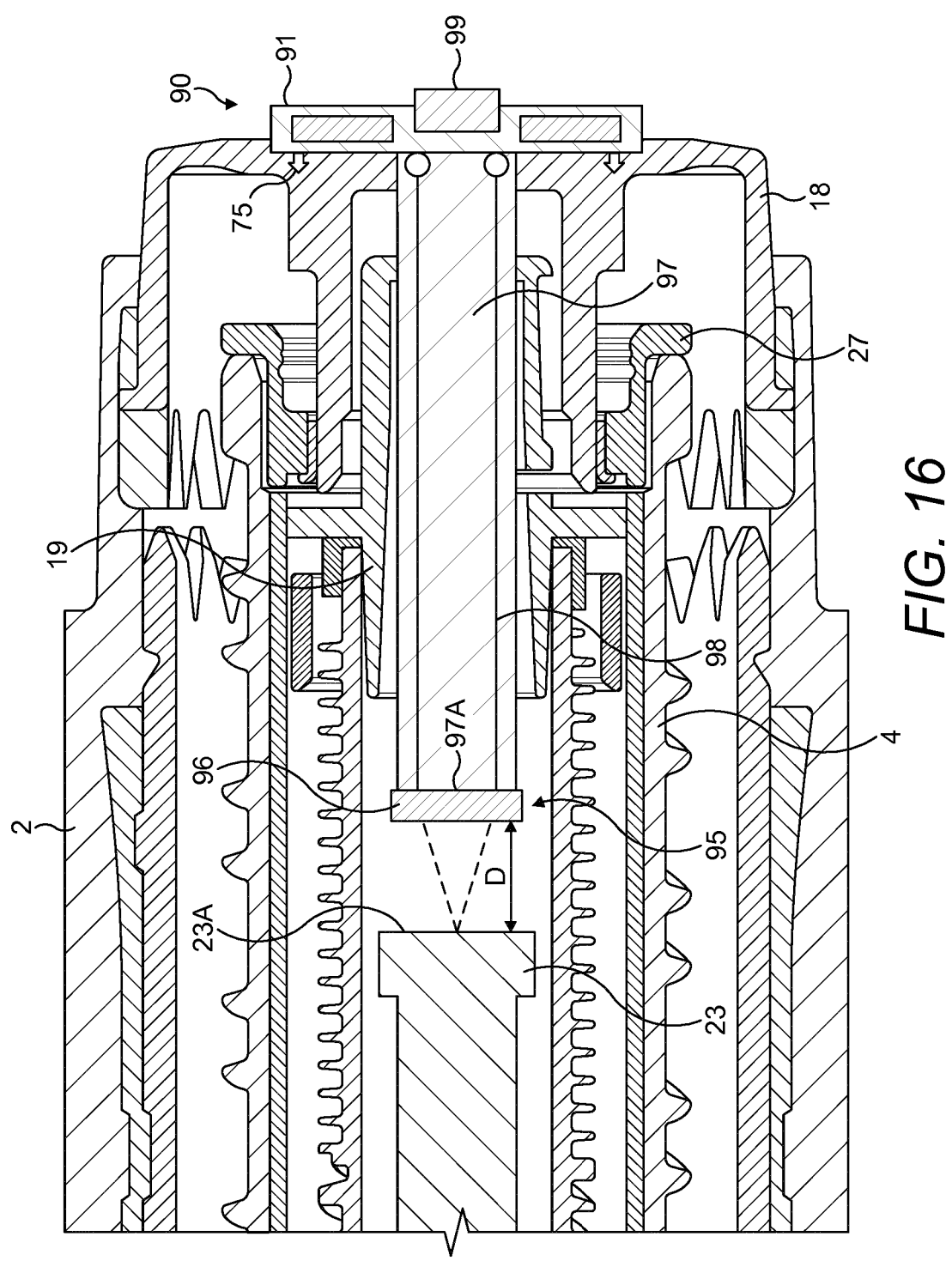
FIG. 16 is a cross-sectional side view of part of a medicament delivery system according to a third embodiment of the disclosure.

Referring now to FIG. 16, a medicament delivery system according to a third embodiment of the disclosure is shown. The medicament delivery system is similar to the measurement delivery system described above in reference to the first embodiment of the disclosure, with like features retaining the same reference numerals. The medicament delivery system comprises a medicament delivery device 1 and a dosage measurement system 90.

The medicament delivery device 1 is in the form of an injection device 1. The dosage measurement system 90 comprises a dosage measurement device 90 that is attached to a proximal end of the injection device 1. The dosage measurement device 90 comprises a housing 91, a processor (not shown), computer readable memory media (not shown), a power switch 99, a battery (not shown), and an output (not shown).

A difference between the dosage measurement system 60 of the first embodiment and the dosage measurement system 90 of the third embodiment is that the sensor unit 65 is omitted and is replaced by an alternative sensor unit 95. The sensor unit 95 comprises a sensor 96, which in the present embodiment is an acoustic sensor 96 having an acoustic source (not shown) and an acoustic detector (not shown). The acoustic sensor 96 is located on a support member 97. In the present embodiment, the acoustic sensor 97 comprises a piezoelectric acoustic sensor 97 having one or more piezoelectric transducers (not shown) to generate and/or detect an acoustic signal.

The support member 97 extends from the housing 91 such that when the dosage measurement device 90 is attached to the injection device 1, the support member 97 extends axially in the distal direction such that an end 97A of the support member 97 is located within the drive sleeve 21. The sensor 96 is mounted on, or proximate to, said end 97A such that the sensor 96 is directed towards the end surface 23A of the lead screw 23. More specifically, the sensor 96 is arranged such that a signal transmitted by the sensor 96 is reflected by the end surface 23A, and the reflected signal is detected by the sensor 96.

The sensor 96 is connected to the processor (not shown) by one or more conductive elements 98, for example, tracks or wires, which extend from the sensor 96 to the housing 91. The conductive elements 98 may be adhered to or embedded in the support member 97.

As described previously, the processor (not shown) is configured to determine a dosage dispensed from the injection device 1 based on a characteristic of the reflected signal detected by the sensor 96, wherein the characteristic of the signal is dependent on the distance D between the sensor unit 95 and the end surface 23A of the lead screw 23. For example, the processor may be configured to determine the dosage dispensed from the injection device 1 based on a detected time delay between a pulse or time varying signal being transmitted by the sensor 96, and the reflected signal being received by the sensor 96. Alternatively, or additionally, the processor may be configured to determine the dosage dispensed from the injection device 1 based on attenuation of the signal.

In the above described embodiments, the button 18 includes an aperture 71 to allow for the dosage measurement device 60 to be inserted into the space 72 of the button 18. However, it should be recognised that in alternative embodiments (not shown) the aperture 71 is omitted. For example, the dosage measurement system 60, 80, 90 may be integrated into the injection device 1 such that the dosage measurement system 60, 80, 90 is permanently received in the space 72 or in a different component of the injection device 1.

In some embodiments (not shown), the dosage measurement system 60, 80, 90 is removably attached or permanently fixed to a part of the injection device 1 other than the button 18, for instance, the housing 3.

In the above described embodiments the attachment formations 74, 75 are in the form of projections 74 on the housing 61, 81, 91 of the dosage measurement device 60, 80, 90 that are received in respective recesses 75 in the button 18. However, it should be recognised that other types of engaging attachment formations or attachment methods may be used. In one alternative embodiment (not shown), the attachment formations are in the form of projections on the button 18 that are received in respective recesses in the housing 61, 81, 91 of the dosage measurement device 60, 80, 90. Alternatively, the dosage measurement system 60, 80, 90 may be bonded to the injection device 1. In one embodiment (not shown), the dosage measurement system 60, 80, 90 is permanently integrated with the injection device 1. For instance, the dosage measurement system 60, 80, 90 may be integrated with the injection device 1 during manufacture of the injection device 1. In one embodiment, the housing 61, 81, 91 of the dosage measurement system 60, 80, 90 is omitted and instead one or more components of the injection device 1, for example, the button 18, drive sleeve 21 and/or housing 3, contain the components of the dosage measurement system 60, 80, 90.

Figure 17:
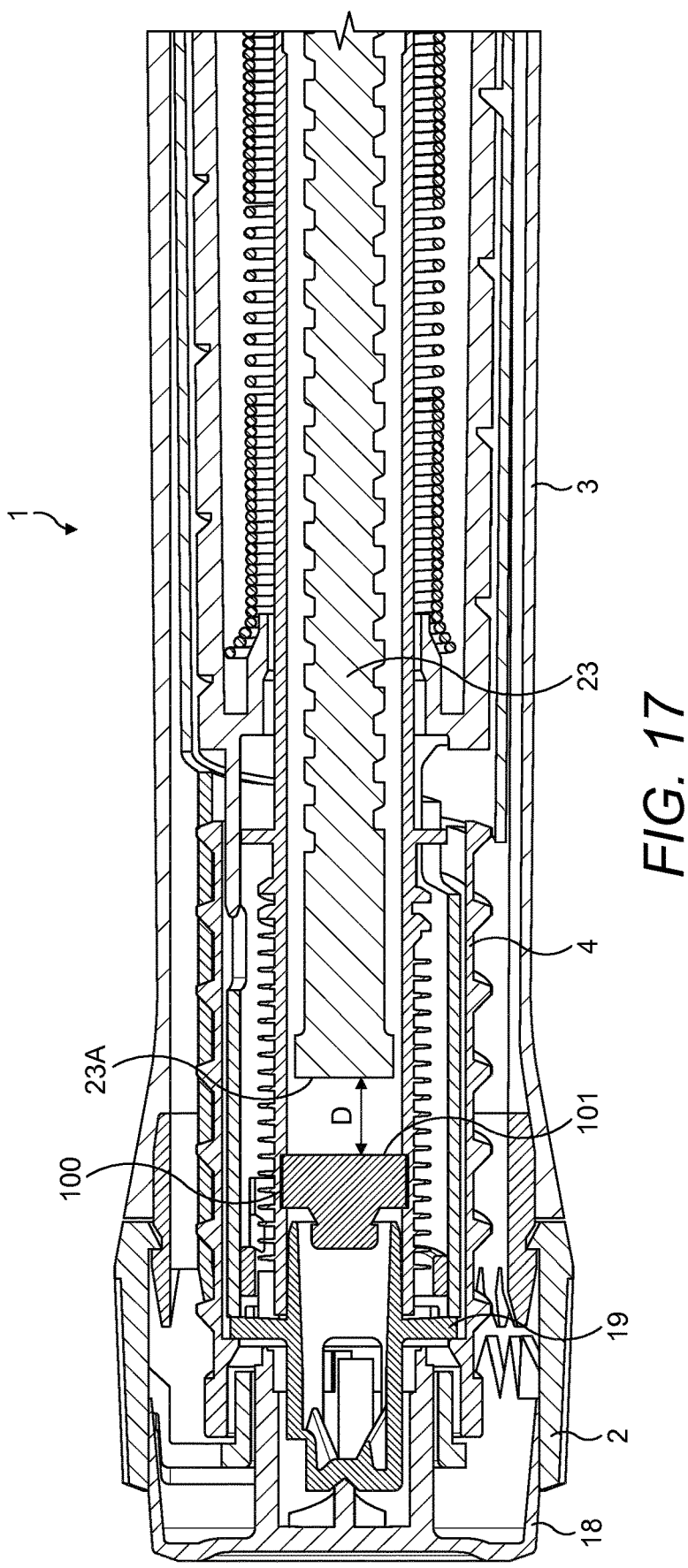
FIG. 17 is a cross-sectional side view of part of a medicament delivery system according to a fourth embodiment of the disclosure; and, FIG. 18 is a schematic cross-sectional side view of part of a medicament delivery system according to a fifth embodiment of the disclosure.

Referring now to FIG. 17, a medicament delivery system according to a fourth embodiment of the disclosure is shown. The medicament delivery system is similar to the measurement delivery system described above in reference to the second embodiment of the disclosure, with like features retaining the same reference numerals. The medicament delivery system comprises a medicament delivery device 1 and a dosage measurement system 100.

The medicament delivery device 1 is in the form of an injection device 1. A difference between the dosage measurement system 80 of the second embodiment and the dosage measurement system 100 of the fourth embodiment is that dosage measurement system 100 is integrated with the injection device 1. In the present embodiment, the dosage measurement system 100 is attached to the inside of the drive sleeve 21. However, it should be recognised that the dosage measurement system 100 may alternatively be mounted to one or more other components of the injection device 1, for example, the housing 3, button 18 and/or clutch plate 19.

In some embodiments (not shown), the housing 101 is integrally formed with a component of the injection device 1, for example, the housing 3, button 18 and/or clutch plate 19.

As before, the dosage measurement system 100 comprises a sensor unit (not shown), battery (not shown), processor (not shown), computer readable media (not shown), and user interface (not shown), for example, a buzzer. The sensor unit is configured to transmit a signal that is reflected by an end surface 23A of the lead screw 23, whereby the reflected signal is detected by the sensor unit. The processor (not show) may be configured to determine a dosage dispensed from the injection device 1 based on a characteristic of the reflected signal detected by the sensor unit.

The dosage measurement system 100 comprises a housing 101 that contains one or more of the components of the dosage measurement system 100. However, it should be recognised that in some embodiments (not shown) the housing may be omitted such that said components of the dosage measurement system 100 are mounted directly to the injection device 1.

While the above described embodiments utilise an optical or acoustic sensor, other types of sensors may be used as well as, or instead of, optical or acoustic sensors. For example, the sensor may include a magnetic sensor, such as a Hall Effect sensor. In such an example, one or more magnets (not shown) may be mounted on, or towards, the proximal end of the lead screw 23 so that axial movement of the lead screw 23 results in a varying magnetic field that is detected by the sensor. In another example, a capacitive sensor may be used, wherein an element is provided on the lead screw 23 that affects the capacitance between two plates provided in the sensor unit. In other examples, mechanical sensors, with mechanical switches and/or tracks, may be used to detect the relative movement of lead screw 23 relative to a component of the injection device 1 such as the housing 3 or drive sleeve 21. In some embodiments (not shown), the sensor unit comprises multiple sensors of one or more types.

In yet another embodiment (not shown), the dosage measurement system includes a sensor unit which comprises an ultrasonic transducer. The ultrasonic transducer may optionally be mounted to an exterior part of the injection device 1, for example, the proximal surface 18A of the button 18. The ultrasonic transducer is configured to transmit ultrasonic waves that travel through the button 18 and are then reflected by the end surface 23A of the lead screw 23, the reflected ultrasonic waves being detected by the ultrasonic transducer or another ultrasonic sensor. The processor (not shown) is configured to determine a dosage dispensed from the injection device 1 based on a characteristic of the reflected signal detected by the ultrasonic transducer, wherein the characteristic of the signal is dependent on the distance D between the ultrasonic transducer and the end surface 23A of the lead screw 23. For example, the processor may be configured to determine the dosage dispensed from the injection device 1 based on a detected time delay between an ultrasonic signal being transmitted by the ultrasonic transducer, and the reflected signal being received by the ultrasonic transducer. Alternatively, or additionally, the processor may be configured to determine the dosage dispensed from the injection device 1 based on attenuation of the ultrasonic signal. Advantageously, the ultrasonic transducer may be fitted to existing medicament delivery devices without requiring modification to the medicament delivery device. This is because the ultrasonic signal can travel through components and thus it is not necessary to provide any apertures in the components of the medicament delivery device to facilitate the signal travelling between the transducer and the lead screw. This may also be possible if, for example, a magnetic sensor is used and the components of the medicament delivery device are manufactured from, for example plastic, apart from a magnet provided on the lead screw that is detected by the magnetic sensor.

Figure 18:
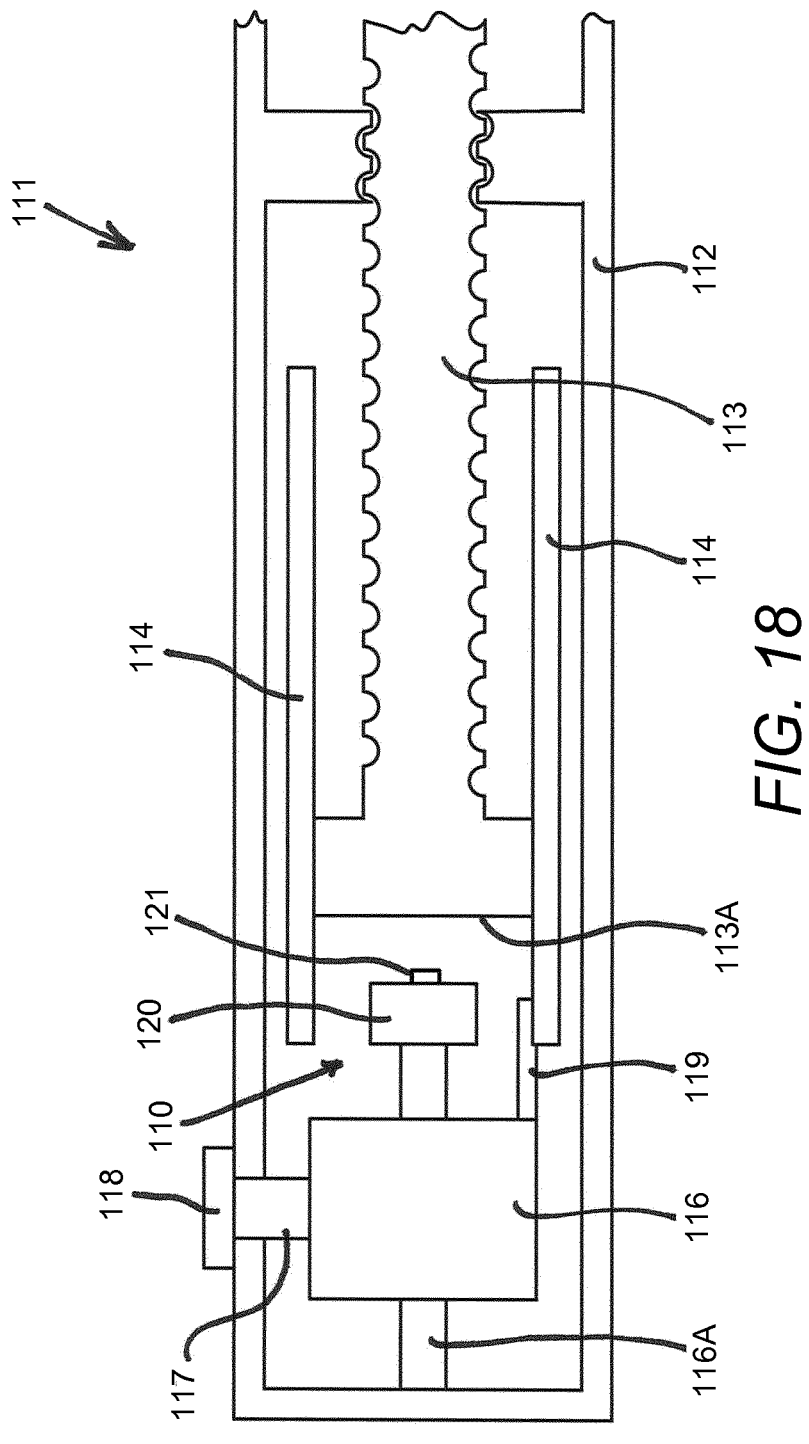

Referring now to FIG. 18, a schematic view of a medicament delivery system according to a fifth embodiment of the disclosure is shown. The medicament delivery system comprises a medicament delivery device 111 and a dosage measurement system 110.

The medicament delivery device 111 is in the form of an injection device 111. The medicament delivery device 111 comprises a housing 112 that contains a medicament reservoir (not shown) and a dispensing mechanism comprising a plunger (not shown), a dispensing member in the form of a lead screw 113, a drive sleeve 114 and a drive unit 115.

The drive unit 115 is configured to rotate the drive sleeve 114 relative to the housing 112. The drive sleeve 114 engages with the lead screw 113 such that rotation of the drive sleeve 114 causes rotation of the lead screw 113. The lead screw 113 and drive sleeve 114 may engage via, for example, a threaded interface (not shown).

The lead screw 113 engages with the housing 112 such that rotation of the lead screw 113 relative to the housing 112 causes axial displacement of the lead screw 113 relative to the housing 112 such that the plunger is moved within the medicament reservoir to dispense medicament therefrom. Thus, operation of the drive unit 115 causes rotation of the drive sleeve 114 such that the lead screw 113 is moved axially relative to the housing 112 to dispense medicament from the medicament reservoir.

The drive unit 115 comprises a biasing member 116 and a locking mechanism 117 that is coupled to an actuator 118. The biasing member 116 is configured to bias the drive sleeve 114 to rotate relative to the housing 112. The biasing member 116 is mounted to an axle 116A such that a first end of the biasing member 116 is connected to the axle 116A. A second end of the biasing member 116 is coupled to the drive sleeve 114 by a connecting member 119. In the present embodiment, the connecting member 119 is fixed relative to the second end of the biasing member 116 and is received in a groove (not shown) in the inside surface of the drive sleeve 114 such that the connecting member 119 is rotationally fixed relative to the drive sleeve 114.

The locking mechanism 117 initially prevents the biasing member 116 from rotating the drive sleeve 114 relative to the housing 112. The locking mechanism 117 is coupled to the actuator 118 such that the actuator 118 is operable to release the drive sleeve 114. The locking mechanism 117 may comprise, for example, a locking pin (not shown) that initially engages the second end of the biasing member 116 to prevent movement of the biasing member 116 relative to the housing 112. Actuation of the actuator 118 by the user may move the locking pin out of engagement with the second end of the biasing member 116. However, the locking mechanism may have a different arrangement, for example, in one embodiment (not shown) comprising an electromagnetic latch that is operated to release the biasing member.

To operate the medicament delivery device 111, the user actuates the actuator 118 such that the locking mechanism 117 releases the biasing member 116 and thus the drive sleeve 114 is rotated relative to the housing 112. This causes the lead screw 113 to be rotated relative to the housing 112 and moved axially relative to the housing 112 such that the plunger (not shown) is moved axially within the medicament reservoir and thus medicament is dispensed therefrom.

The medicament reservoir may be fluidly connected to, for example, a needle, for delivery of the medicament to a patient.

The dosage measurement system 110 comprises a sensor unit 120 having a sensor 121 and a processor (not shown). In the present embodiment the sensor 121 is an optical sensor 121 having a light source (not shown) and a light detector (not shown). In the present embodiment, the sensor unit 120 is mounted to the axle 116A that supports the biasing member 116. However, it should be recognised that in alternative embodiments (not shown) the sensor unit 120 is mounted to a different part of the medicament delivery device 111, for example, the housing 112.

The sensor 121 is configured to transmit a signal that is reflected by an end surface 113A of the lead screw 113, whereby the reflected signal is detected by the sensor 121. In some embodiments (not shown), the sensor unit 120 further comprises a transmission member (not shown), such as a light guide, that transmits a signal from the sensor 121 towards the end surface 113A of the lead screw 113.

The processor (not shown) is configured to determine a dosage dispensed from the injection device 111 based on a characteristic of the reflected signal detected by the sensor unit 120, wherein the characteristic of the signal is dependent on the distance between the sensor unit 120 and the end surface 113A of the lead screw 113. For example, the processor may be configured to determine the dosage dispensed from the injection device 111 based on a detected time delay between a pulse or time varying signal being transmitted by the sensor 121, and the reflected signal being received by the sensor 121. Alternatively, or additionally, the processor may be configured to determine the dosage dispensed from the injection device 111 based on attenuation of the signal.

In an alternative embodiment (not shown), the sensor 121 is instead directed towards a different part of the lead screw 113 such that such that the sensor 121 detects the axial displacement of said different part of the lead screw 113. For example, the sensor 121 may configured to transmit a signal that is reflected by distally-facing surface (not shown) of the lead screw 113, whereby the reflected signal is detected by the sensor 121. In one such embodiment, the lead screw 113 moves towards the sensor 121 as the medicament is dispensed such that the distance between the sensor 121 and the surface of the lead screw decreases.

In another embodiment (not shown), the sensor 121 is configured to transmit a signal that is reflected by a component of the drive mechanism other than the lead screw 113. For example, the drive sleeve 114 may comprise the dispensing member, the sensor 121 being configured to transmit a signal that is reflected by the drive sleeve 114 to detect axial displacement of the drive sleeve 114. The processor (not shown) is configured to determine a dosage dispensed from the injection device 111 based on a characteristic of the reflected signal detected by the sensor unit 120, wherein the characteristic of the signal is dependent on the distance between the sensor unit 120 and the drive sleeve 114. Alternatively, the dispensing member may comprise a plunger rod (not shown) that connects the lead screw 113 to a piston within the medicament reservoir, the sensor 121 being configured to transmit a signal that is reflected by the plunger rod to detect axial displacement of the plunger rod. The processor (not shown) is configured to determine a dosage dispensed from the injection device 111 based on a characteristic of the reflected signal detected by the sensor unit 120, wherein the characteristic of the signal is dependent on the distance between the sensor unit 120 and the plunger rod.

In the present embodiment, the biasing member 116 is in the form of a torsion spring 116. However, it should be recognised that other types of biasing member are intended to fall within the scope of the disclosure. In yet further embodiments (not shown), the biasing member is omitted and instead the drive unit comprises an electric motor that is operated to rotate the drive sleeve and thus dispense the medicament from the medicament reservoir. Alternatively, the drive unit may comprise a component that is manually rotated by the user to rotate the drive sleeve to dispense the medicament.

In some embodiments (not shown), the lead screw 13, 113 and drive sleeve 21, 114 are omitted and instead the drive mechanism has a different arrangement of dispensing member that moves axially within the housing 3, 112 to dispense medicament from the medicament reservoir. For instance, the drive mechanism may comprise a coil spring that is configured to bias a dispensing member axially within the housing to dispense medicament from the medicament reservoir. The dispensing member comprises a rod that is coupled to a piston or plunger within the medicament reservoir. A locking mechanism initially holds the coil spring in a compressed position to prevent the coil spring from moving the rod within the housing to dispense medicament. The user presses an actuator to release the locking mechanism such that the coil spring is released to move the rod axially within the housing to dispense medicament. The sensor unit is configured to detect the axial movement of the dispensing member, which in this embodiment is the rod. More specifically, the sensor is configured to transmit a signal that is reflected by a part of the rod, wherein the reflected signal is detected by the sensor to detect axial displacement of the rod. The processor is configured to determine a dosage dispensed from the injection device 1, 111 based on a characteristic of the reflected signal detected by the sensor unit, wherein the characteristic of the signal is dependent on the distance between the sensor unit and the rod.

In some embodiments (not shown), the dosage measurement system 60, 80, 90, 100, 110 comprises a first part and a second part that is attachable to the first part. The second part may be releasably attachable to the first part. The first part of the dosage measurement device 60, 80, 90, 100, 110 may comprise one or more attachment formations (not shown) that are configured to engage with corresponding attachment formations (not shown) on the second part. The attachment formations of the first part or second part may comprise projections that engage with respective recesses in the other of the first and second part such that the second part can be clipped to the first part. However, it should be recognised that in alternative embodiments (not shown) the second part is attached to the first part via a different arrangement, for example, being received in a recess in the first part such that the first and second parts are held together via friction. Optionally, the first and second parts may comprise engaging elements, for example, rails that engage with grooves, which ensure a particular rotational orientation of the first part relative to the second part when the second part is attached to the first part.

The dosage measurement system 60, 80, 90, 100, 110 comprising first and second parts allows for the first part to be attached to, or integrated with, the injection device 1, 111 and for the second part to be removably attached to the first part. Therefore, the injection device 1, 111 and the first part can be disposed of and the second part can be reused by removing it from the first part and attaching it to the first part of a different injection device 1, 111. One or more of the battery, user interface, communications module, processor and sensor can be incorporated into the second part. Thus, these components, which are relatively expensive, can be reused with further injection devices by attaching the second part to the first part of said further injection devices.

In one embodiment, the first part comprises a transmission member, for example, a light guide, that is fixed to the injection device 1, 111. The second part comprises a battery, processor and a sensor. The second part attaches to the first part such that the transmission member and sensor form a sensor unit, wherein the transmission member is able to transmit a signal emitted by the sensor towards the detection elements and also to transmit the reflected signal back towards the sensor. Once medicament delivery is complete, the second part is detached from the first part and the first part together with the medicament delivery device is disposed of. In another embodiment (not shown), the first part comprises a support member that is fixed to the injection device 1, 111 and a sensor that is provided on the support member. The second part comprises a battery and processor. The second part attaches to the first part such that the sensor is coupled to the processor and thus the processor is able to determine a dosage dispensed from the medicament reservoir based on the measured axial displacement of the displacement member. Once medicament delivery is complete, the second part is detached from the first part and the first part together with the medicament delivery device is disposed of.

In the above described embodiments the medicament delivery device 1, 111 comprises an injection device. The injection device may comprise a pen injection device and may comprise an autoinjector. However, it should be recognised that the medicament delivery system may comprise a different type of medicament delivery device. For example, the medicament delivery device may comprise a patch device that is attached to the injection site of a patient. The medicament delivery device may be a pump device.

While the embodiments above have been described in relation to collecting data from an insulin injector pen, it is noted that embodiments of the disclosure may be used for other purposes, such as monitoring of injections of other medicaments.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "medicament delivery device", which is also referred to hereinafter as "drug delivery device", shall encompass any type of device or system configured to dispense a drug into a human or animal body. Without limitation, a drug or medicament delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminogly-cane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A dosage measurement system for a medicament delivery device, wherein the medicament delivery device comprises a medicament reservoir and a dispensing mechanism comprising a dispensing member that is axially moveable to dispense a medicament from the medicament reservoir, wherein the dispensing member comprises a lead screw and wherein the dispensing mechanism further comprises a drive member that is configured to rotate to axially displace the lead screw relative to the drive member to dispense medicament from the medicament reservoir, the dosage measurement system comprising:

a sensor unit configured to measure an axial displacement of the lead screw, wherein the sensor unit is configured to transmit a signal such that said signal is reflected from the lead screw, the sensor unit configured to detect said reflected signal, wherein the signal is transmitted along a path L1, and the reflected signal is transmitted along a path L2, and the sensor unit is configured to measure the axial displacement based on a linear distance Y between a central axis and path L2; and a processor configured to determine a dosage dispensed from the medicament reservoir based on the measured axial displacement of the lead screw.

2. The dosage measurement system of claim 1, wherein the sensor unit comprises a transmission member, the signal being transmitted through the transmission member.

3. The dosage measurement system of claim 2, wherein the transmission member comprises a light guide.

4. The dosage measurement system of claim 1, wherein the sensor unit is configured to transmit a signal that travels within the drive member.

5. The dosage measurement system of claim 1, wherein the sensor unit is integrated with the medicament delivery device.

6. The dosage measurement system of claim 1, wherein the sensor unit is removably attachable to the medicament delivery device.

7. The dosage measurement system of claim 1, wherein the medicament delivery device comprises an actuator that is actuatable by a user to dispense the medicament, and wherein the sensor unit is configured to be mounted to the actuator.

8. The dosage measurement system of claim 7, wherein the actuator comprises a space, and wherein the sensor unit is configured to be at least partially received in the space.

9. The dosage measurement system of claim 7, wherein the processor determines the dosage dispensed from the medicament reservoir when the actuator is actuated.

10. The dosage measurement system of claim 9, wherein the processor does not determine the dosage dispensed from the medicament reservoir until the actuator is actuated.

11. The dosage measurement system of claim 7, wherein the actuator is configured to move from a first position to a second position upon actuation, and wherein the sensor unit is configured to be mounted to the actuator to move with the actuator between the first and second positions.

12. The dosage measurement system of claim 1, wherein the dosage measurement system comprises a first part configured to be fixed to a medicament delivery device and a second part that is removably attachable to the first part.

13. The dosage measurement system of claim 12, wherein the second part comprises the processor.

14. The dosage measurement system of claim 12, wherein the first part comprises a transmission member of the sensor unit.

15. The dosage measurement system of claim 12, wherein the first part and the second part comprise engaging elements configured to ensure a rotational orientation of the first part relative to the second part when the second part is attached to the first part.

16. A medicament delivery system, comprising:

a medicament delivery device comprising a medicament reservoir and a dispensing mechanism comprising a dispensing member that is axially moveable to dispense a medicament from the medicament reservoir, wherein the dispensing member comprises a lead screw and wherein the dispensing member further comprises a drive member that is configured to rotate to axially displace the lead screw relative to the drive member to dispense medicament from the medicament reservoir; and a dosage measurement system comprising:

a sensor unit configured to measure an axial displacement of the lead screw, the sensor unit being configured to transmit a signal such that said signal is reflected from the lead screw, the sensor unit configured to detect said reflected signal, wherein the signal is transmitted along a path L1, and the reflected signal is transmitted along a path L2, and the sensor unit is configured to measure the axial displacement based on a linear distance Y between a central axis and path L2; and a processor configured to determine a dosage dispensed from the medicament reservoir based on the measured axial displacement of the lead screw.

17. The medicament delivery system of claim 16, wherein the medicament reservoir contains the medicament.

18. The medicament delivery system of claim 16, wherein the sensor unit comprises a transmission member, the signal being transmitted through the transmission member.

* * * * *